US008961996B2

(12) United States Patent
Borca et al.

(10) Patent No.: US 8,961,996 B2
(45) Date of Patent: Feb. 24, 2015

(54) ***N*-LINKED GLYCOSYLATION ALTERATION IN E0 AND E2 GLYCOPROTEIN OF CLASSICAL SWINE FEVER VIRUS AND NOVEL CLASSICAL SWINE FEVER VIRUS VACCINE**

(75) Inventors: Manuel Borca, Westbrook, CT (US); Guillermo Risatti, Westbrook, CT (US)

(73) Assignees: The United States of America, as represented by the Secretary of Agriculture, Washington, DC (US); The University of Connecticut, Famington, CT (US)

( * ) Notice: Subject to any disclaimer, the term of this patent is extended or adjusted under 35 U.S.C. 154(b) by 598 days.

(21) Appl. No.: 12/913,329

(22) Filed: Oct. 27, 2010

(65) Prior Publication Data

US 2011/0038886 A1 Feb. 17, 2011

Related U.S. Application Data

(62) Division of application No. 12/288,915, filed on Oct. 24, 2008, now abandoned.

(51) Int. Cl.

| | |
|---|---|
| ***A61K 39/12*** | (2006.01) |
| ***G01N 33/569*** | (2006.01) |
| ***A61K 39/187*** | (2006.01) |
| ***C07K 14/005*** | (2006.01) |
| ***C12N 7/00*** | (2006.01) |
| ***C12Q 1/70*** | (2006.01) |
| *C12N 15/33* | (2006.01) |
| *A61K 39/00* | (2006.01) |

(52) U.S. Cl.

CPC .......... *G01N 33/56983* (2013.01); *A61K 39/12* (2013.01); *A61K 39/187* (2013.01); *A61K 2039/5254* (2013.01); *C07K 14/005* (2013.01); *C12N 7/00* (2013.01); *C12N 2770/24322* (2013.01); *C12N 2770/24362* (2013.01); *C12Q 1/701* (2013.01); *G01N 2333/183* (2013.01)

USPC .................................... 424/220.1; 435/91.42

(58) Field of Classification Search

CPC ........... C12N 2770/24361; C12N 2770/24362; C12N 15/62; C12N 9/506; C12N 2770/24334; C12N 2760/18022; C12N 2760/18561; C12N 2770/10034; C12N 2770/24162; C12N 2770/24321; A61K 2039/5254; A61K 2039/53

See application file for complete search history.

(56) References Cited

U.S. PATENT DOCUMENTS

| | | | | |
|---|---|---|---|---|
| 8,063,195 | B2 * | 11/2011 | Borca et al. | 536/23.72 |
| 8,114,852 | B2 * | 2/2012 | Borca et al. | 514/44 R |
| 8,133,495 | B2 * | 3/2012 | Borca et al. | 424/211.1 |

OTHER PUBLICATIONS

Risatti et al. (A) J. Virol. .2007, vol. 81, No. 2, pp. 924-933.*
Risatti et al. (B) Virol. .2006, vol. 355, pp. 94-101.*
Risatti et al. (C) J. Virol. (J. Virol. 2005, vol. 79, No. 6, pp. 3787-3796.*
Sainz et al. Virology. Available on line on Sep. 2007, vol. 370, Issue 1, pp. 122-129.*

* cited by examiner

*Primary Examiner* — Bao Li
(74) *Attorney, Agent, or Firm* — John D. Fado; Evelyn M. Rabin

(57) ABSTRACT

E2 is one of the three envelope glycoproteins of Classical Swine Fever Virus (CSFV). E2 is involved in several functions including virus attachment and entry to target cells, production of antibodies, induction of protective immune response in swine, and virulence. Seven putative glycosylation sites in E2 were modified by site directed mutagenesis of a CSFV Brescia infectious clone (BICv). A panel of virus mutants was obtained and used to investigate whether the removal of putative glycosylation sites in the E2 glycoprotein would affect viral virulence/pathogenesis in swine. We observed that rescue of viable virus was completely impaired by removal of all putative glycosylation sites in E2, but restored when mutation N185A reverted to wild-type asparagine produced viable virus that was attenuated in swine. Single mutations of each of the E2 glycosylation sites showed that amino acid N116 (N1v virus) was responsible for BICv attenuation. N1v efficiently protected swine from challenge with virulent BICv at 3 and 28 days post-infection suggesting that glycosylation of E2 could be modified for development of CSF live-attenuated vaccines. Additionally, a new developed virus, contained deletions of putative glycosylation sites N1 in E2 and N1 in E0 (6b), called N1E0/2v, induce a solid protection against the challenge at 3 and 28 days post-inoculation.

9 Claims, 6 Drawing Sheets
(1 of 6 Drawing Sheet(s) Filed in Color)

O1 N1 N2 N3 N4 N5 N6

| | Relative virus yield |
|---|---|
| BICv E2 | 1.00 |
| O1v | 1.02 |
| N1v | 1.08 |
| N2v | 1.02 |
| N3v | 0.91 |
| N4v | 1.04 |
| N5v | 1.02 |
| N6v | 0.93 |
| ΔO1N1-N6/N3v | 0.76 |
| ΔO1N1-N6 | Non viable |
| N4N5v | 0.96 |
| O1N1v | 0.98 |
| O1N1N2v | 1.01 |
| O1N1N2N3 | Non viable |
| N1N2N3 | Non viable |
| N3N4N5 | Non viable |

A

B

A 8
7
6
5
4
3
2
1
0
log 10 TCID50/ml
0 4 8 24 48 72
Hours post-infection
O1v N1v N2v N3v N4v N5v N6v BICv

B 8
7
6
5
4
3
2
1
0
log 10 TCID50/ml
0 24 48 72
Hours post-infection
N4N5v O1N1N2v O1N1-N6/N3v BICv O1N1v

A

O1v N1v N2v N3v N4v N5v N6v ΔO1N1-N6/N3v N4N5v BICv 85 kDa 39 kDa

B

BICv O1v O1N1v N1v O1N1N2v N2v BICv N4v N4N5v N5v BICv 85 kDa 39 kDa

C 1 2 3

175 kDa 83 kDa 62 kDa 47.5 kDa

D 1 2 3

129 kDa 85 kDa 39 kDa

A

B

SEQUENCE LISTING

<160> NUMBER OF SEQ ID NOS: 11

<210> SEQ ID NO 1
<211> LENGTH: 12297
<212> TYPE: DNA
<213> ORGANISM: Classical Swine Fever Virus

<400> SEQUENCE: 1

```
gtatacgagg ttagttcatt ctcgtgtaca tgattggaca aatcaaaatc tcaatttggt     60

tcagggcctc cctccagcga cggccgagct gggctagcca tgcccacagt aggactagca    120

aacggaggga ctagccgtag tggcgagctc cctgggtggt ctaagtcctg agtacaggac    180

agtcgtcagt agttcgacgt gagcagaagc ccacctcgag atgctatgtg gacgagggca    240

tgcccaagac acaccttaac cctagcgggg gtcgttaggg tgaaatcaca ccatgtgatg    300

ggagtacgac ctgatagggt gctgcagagg cccactatta ggctagtata aaaatctctg    360

ctgtacatgg cacatggagt tgaatcattt tgaactttta tacaaaacaa acaaacaaaa    420

accaatggga gtggaggaac cggtatacga tgtaacgggg agaccattgt ttggagaccc    480

aagtgaggta cacccacaat caacattgaa gctaccacat gataggggga gaggcaacat    540

caaaacaaca ctgaagaacc tacctaggag aggtgactgc aggagtggca accacctagg    600

cccggttagt gggatatatg taaagcccgg ccctgtcttt tatcaggact acatgggccc    660

agtctatcat agagcccctc tagagttttt tgacgaagca cagttttgtg aggtgaccaa    720

aaggataggt agggtgacag gtagtgacgg aaagctttac catatatacg tgtgcatcga    780

tggttgcatc ctgctgaagc tagccaagag gggcgagcca agaaccctga agtggattag    840

aaatctcacc gactgtccat tgtgggttac cagttgttct gatgatggtg caagtgcaag    900

taaagagaag aaaccagata ggatcaacaa gggtaaatta aagatagccc caaaagagca    960

tgagaaggac agcaggacta agccacctga tgctacgatt gtagtggaag gagtaaaata   1020

ccaggtcaaa aagaaaggta aagttaaggg aaagaatacc caagacggcc tgtaccacaa   1080

caagaataaa ccaccagaat ctaggaagaa attagaaaaa gccctattgg catgggcagt   1140

gatagcaatt atgttatacc aacctgttgc agccgaaaat ataactcaat ggaacctgag   1200

tgacaacggt accaatggta tccagcacgc tatgtacctt agaggagtca gcagaagctt   1260
```

-continued

```
gcatgggatc tggccagaaa aaatatgcaa aggagtcccc acctacctgg ccacagacac   1320
ggaactgaga gaaatacagg gaatgatgga tgccagcgag gggacaaact atacgtgctg   1380
taagttacag agacatgaat ggaacaaaca tggatggtgt aactggtata acatagaccc   1440
ctggatacag ttgatgaata gaacccaagc aaacttggca gaaggccctc cgagcaagga   1500
gtgcgccgtg acttgcaggt acgataaaaa tgctgacatt aacgtggtca cccaggccag   1560
aaacaggcca accaccctaa ctggctgcaa gaaagggaaa aatttttctt ttgcgggtac   1620
agttatagag ggcccatgta atttcaacgt ttctgttgag gatatcttat atggggatca   1680
tgagtgtggc agtctactcc aggatacggc tctataccta gtagatggaa tgaccaacac   1740
tatagagaga gccaggcagg gagccgcgag ggtgacatct tggctaggga ggcaactcag   1800
aactgccggg aagaggttgg agggcagaag caaaacctgg tttggtgcct atgccctatc   1860
accttattgt aatgtgacaa gcaaaatagg gtacatatgg tacactaaca actgtacccc   1920
ggcttgcctc cccaaaaata caaagataat aggccccggt aaatttgaca ctaacgcgga   1980
agacggaaag attctccatg agatgggggg ccacctatca gaatttctgc tgctctctct   2040
ggtcgttctg tctgacttcg cccctgaaac agccagcgcg ttatacctca ttttgcacta   2100
cgtgatccct caatcccatg aagaacctga aggctgtgac acaaaccagc tgaatttaac   2160
agtggaactc aggactgaag acgtgatacc atcatcagtc tggaatgttg gcaaatatgt   2220
gtgtgttaga ccagactggt ggccatatga aaccaaggtg gctttgttat ttgaagaggc   2280
aggacaggtc gtaaagttag ccttgcgggc actgagggat ttaaccaggg tctggaatag   2340
cgcatcaacc acggcattcc tcatctgctt gataaaagta ttaagaggac aggtcgtgca   2400
aggtgtgata tggctgttac tggtaactgg ggcacaaggc cggctagcct gcaaggaaga   2460
tcacaggtac gctatatcaa caaccaatga gatagggcta cttggggccg aaggtctcac   2520
taccacctgg aaagaataca accacaattt gcaactggat gatgggaccg tcaaggccat   2580
ctgcatggca ggttccttta aagtcacagc acttaatgtg gttagtagga ggtatctggc   2640
atcattacat aaggacgctt tagccacttc cgtgacattc gagctcctgt tcgacgggac   2700
cagcccattg accgaggaaa tgggagatga cttcgggttc ggactgtgtc cgtatgatac   2760
gagccctgta gtcaagggaa agtacgccac aaccttgttg gctggtagtg cattctacct   2820
agtttgccca atagggtgga cgggtgttat agagtgcacg gcagtgagcc cgacaactct   2880
gagaacagaa gtggtaaaga ccttcagaag agagaaaccc tttccgtaca gaagggattg   2940
tgtgaccact acagtggaaa atgaagatct attctactgt aaatgggggg gcaattggac   3000
atgtgtgaaa ggtgaaccag tgacctacac ggggggggcca gtaaaacaat gcagatggtg   3060
tggcttcgac ttcaatgagc ctgacggact cccacactac cccataggta agtgcatttt   3120
ggcagctgag acaggttaca gaatagtgga ttcaacggac tgtaacagag atggcgttgt   3180
aatcagcaca gaggggagtc atgagtgctt gattggtgcc acaactgtca aggtgcatgc   3240
attagatgaa agactaggcc ctatgccatg caggcctaag gagatcgtct ctagtgcggg   3300
acctgtaagg aaaacttcct gtacattcgc ctacgcaaaa actctgagga acaggtatta   3360
tgagcccagg gacagctatt tccaacaata tatgctcaag ggcgagtatc agtactggtt   3420
tgatctggat gtgaccgacc gccactcaga ttacttcgca gaattcattg tcttggtggt   3480
ggtggcactg ttgggaggaa gatatgtcct gtggctaata gtgacctaca tagttctaac   3540
agaacaactc gccgctggtc tacagttagg ccagggtgag gtagtgttaa tagggaactt   3600
aatcacccac acagatattg aggttgtagt atatttctta ctgctctatt tggtcatgag   3660
```

```
agatgagcct ataaagaaat ggatactact gctgttccat gctatgacca acaatccagt   3720
taagaccata acagtggcac tgctcatggt tagcggggtt gccaagggtg gaaagataga   3780
tggtggttgg cagcggctgc cggagaccaa ctttgatatc caactcgcgc tgacagttat   3840
agtagtcgct gtgatgttgc tggcaaagaa agatccgact accgtcccct tggttataac   3900
ggtggcaacc ctgagaacgg ctaagataac taatggactt agtacagatc tagccatagc   3960
tacagtgtca acagctttgc taacctggac ctacattagt gactattata aatacaagac   4020
cttgctacag taccttatta gcacagtgac aggtatcttc ttgataaggg tactgaaggg   4080
ggtaggtgag ttagatttac acaccccaac cttaccatct tacagacccc tcttcttcat   4140
cctcgtgtac ctcatttcca ctgcagtggt aacaagatgg aatctggaca tagccggatt   4200
gctgctgcag tgtgtcccaa cccttttaat ggttttcacg atgtgggcag acatccttac   4260
cctgatcctc atactgccta cttacgagtt gacaaaacta tattacctca aggaagtgaa   4320
gattggggca gaaaggggct ggttgtggaa gaccaacttc aagagggtaa atgacatata   4380
cgaagttgac caagctggtg agggggtgta ccttttccca tcaaaacaaa agacaggtac   4440
aataacaggt actatgttgc cattgatcaa agccatactc ataagttgca tcagcaataa   4500
gtggcaattt atatatctat tgtacttgat attcgaagtg tcttactacc ttcacaagaa   4560
gatcatagat gaaatagcag gagggaccaa cttcatctcg agacttgtag ccgctctgat   4620
tgaagccaat tgggcctttg acaacgaaga agttagaggt ttaaagaagt tcttcctgct   4680
gtctagtagg gttaaagaac tgatcatcaa acacaaagtg aggaatgaag tgatggtcca   4740
ctggtttggc gacgaagagg tctatgggat gccgaagctg gttggcttag tcaaggcagc   4800
aacactgagt aaaaataaac attgtatttt gtgcaccgtc tgtgaaaaca gagagtggag   4860
aggagaaacc tgcccaaaat gcggccgttt tgggccacca gtgacctgtg gcatgaccct   4920
agccgacttt gaagaaaaac actataagag gattttcttt agagaggatc aatcagaagg   4980
gccggttagg gaggagtatg cagggtatct gcaatataga gccagagggc aattattcct   5040
gaggaatctc ccggtgctag caacaaaagt caagatgctc ctggtcggaa atcttgggac   5100
ggaggtgggg gatttggaac accttggctg ggtgctcaga gggcctgccg tttgcaagaa   5160
ggttaccgaa catgagaaat gcaccacatc cataatggac aaattaactg ctttcttcgg   5220
tgttatgcca aggggcacca cacctagagc ccctgtgaga ttccccacct ctctcttaaa   5280
gataagaagg gggctggaaa ctggctgggc gtacacacac caaggtggca tcagttcagt   5340
ggaccatgtc acttgtggga aagacttact ggtatgtgac actatgggcc ggacaagggt   5400
tgtttgccaa tcaaataaca agatgacaga cgagtccgag tatggagtta aaactgactc   5460
cggatgcccg gagggagcta ggtgttacgt gttcaaccca gaggcagtta acatatccgg   5520
gactaaagga gccatggtcc acttacaaaa aactggagga gaattcacct gtgtgacagc   5580
atcagggact ccggccttct ttgatctcaa gaacctcaaa ggctggtcag ggctgccgat   5640
atttgaggca tcaagtggaa gagtagtcgg cagggttaag gtcgggaaga atgaggactc   5700
taaaccaacc aagcttatga gtggaataca aacagtctcc aaaagtacca cagacttgac   5760
agaaatggta aagaaaataa caaccatgaa caggggagaa ttcagacaaa taacccttgc   5820
cacaggtgcc ggaaaaacca cggaactccc tagatcagtc atagaagaga taggaaggca   5880
taagagggtc ttggtcttga tccctctgag ggcggcagca gagtcagtat accaatatat   5940
gagacaaaaa cacccaagca tagcattcaa cttgaggata ggggagatga aggaagggga   6000
```

-continued

```
catggccaca gggataacct atgcctcata tggttacttc tgtcagatgc cacaacctaa   6060
gctgcgagcc gcgatggttg agtactcctt catattcctt gatgagtacc actgtgccac   6120
ccccgaacaa ttggctatca tggaaagat ccacagattt tcagagaacc tgcgggtagt   6180
agccatgacc gcaacaccag caggcacggt aacaactaca gggcaaaaac accctataga   6240
agaatacata gccccagaag tgatgaaggg ggaagactta ggttcagagt acttggacat   6300
agctggacta aagataccag tagaggagat gaagagtaac atgctggtct ttgtgcccac   6360
aaggaacatg gctgtagaga cggcaaagaa actgaaagct aagggttata actcaggcta   6420
ctattatagt ggagaggatc catctaacct gagggtggta acatcacagt ccccgtacgt   6480
ggtggtagca accaacgcaa tagaatcagg tgttactctc ccagacttgg atgtggtcgt   6540
cgacacaggg cttaagtgtg aaaagaggat acggctgtca cctaagatgc ccttcatagt   6600
gacgggcctg aagagaatgg ctgtcacgat tggggaacaa gcccagagaa gggggagagt   6660
tgggagagtg aagcctggga gatactacag gagtcaagaa acccccgttg gttccaaaga   6720
ttaccattac gacctactgc aagcacagag gtacggtata gaagatggga taaacatcac   6780
caaatctttt agagagatga attatgattg gagcctttat gaggaggata gtctgatgat   6840
tacacaattg gaaatcctca acaatctgtt gatatcagaa gagctaccaa tggcagtaaa   6900
aaatataatg gccaggactg accacccaga accaatccaa ctggcgtaca acagctacga   6960
aacgcaggtg ccagtgctat tcccaaaaat aaaaaatgga gaggtgactg acagttacga   7020
taactatacc ttcctcaacg caagaaagct gggggatgat gtacctccct acgtgtatgc   7080
cacagaggat gaggacttag cggtagagct gctgggctta gactggccgg accctgggaa   7140
ccaaggaacc gtggaggctg gtagagcact aaaacaagta gttggtctat caacagctga   7200
gaacgccctg ttagtagctt tattcggcta tgtaggatat caggcactct caaagaggca   7260
tataccagta gtcacagaca tatattcaat tgaagatcac aggttggaag acaccacaca   7320
cctacagtat gccccgaatg ctatcaagac ggaggggaag gagacagaat tgaaggagct   7380
agctcagggg gatgtgcaga gatgtatgga agctatgact aattatgcaa gagatggcat   7440
ccaattcatg aagtctcagg cactgaaagt gaaagaaacc cccacttaca aagagacaat   7500
ggacaccgtg gcggactatg taaagaagtt catggaggca ctggcggaca gcaaagaaga   7560
catcataaaa tatgggttgt gggggacgca cacaacctta tataagagca tcggtgctag   7620
gcttgggaac gagactgcgt tcgctaccct ggtcgtgaaa tggctggcat ttgggggaga   7680
atcaatagca gaccatgtca aacaagcggc cacagacttg gtcgtttact atatcatcaa   7740
cagacctcag ttcccaggag acacggagac acaacaggaa ggaaggaaat ttgtagccag   7800
cctactggtc tcagccctgg ctacttacac ttacaaaagc tggaattaca ataatctgtc   7860
caagatagtt gaaccggctt tggctactct gccctatgcc gccacagctc tcaagctatt   7920
cgcccccact cgattggaga gcgttgtcat actgagtacc gcaatctaca aaacctacct   7980
atcaatcagg cgcggaaaaa gcgatggttt gctaggcaca ggggttagtg cggctatgga   8040
aatcatgtca caaaacccag tatctgtggg tatagcggtc atgctagggg tgggggccgt   8100
agcggcccac aatgcaatcg aagccagtga gcagaagaga acactactca tgaaagtttt   8160
tgtaaagaac ttcttggatc aggcagccac tgatgaatta gtcaaggaga gccctgagaa   8220
aataataatg gctttgtttg aagcagtgca gacagtcggc aaccctctta gactggtata   8280
ccacctttac ggagtttttt acaaagggtg ggaggcaaaa gagttggccc aaaggacagc   8340
cggtaggaat cttttcactt tgataatgtt tgaggctgtg gaactactgg gagtagatag   8400
```

-continued

```
cgaaggaaag atccgccagc tatcaagcaa ttacatacta gagctcctgt ataagttccg   8460
tgacagtatc aagtccagcg tgaggcagat ggcaatcagc tgggcccctg ccccttttag   8520
ttgtgattgg acaccgacgg atgacagaat agggcttccc caagataatt tcctccgagt   8580
ggagacaaaa tgcccctgtg gttacaagat gaaagcagtt aagaattgtg ctggggagtt   8640
gagactctta gaagaggaag gctcatttct ctgcaggaat aaattcggga gaggttcacg   8700
gaactacagg gtgacaaaat actatgatga caatctatca gaaataaagc cagtgataag   8760
aatggaagga catgtggaac tctactacaa gggagccact attaaactgg atttcaacaa   8820
cagtaaaaca atattggcaa ccgataaatg ggaggtcgat cactccactc tggtcagggt   8880
gctcaagagg cacacagggg ctggatatcg tggggcatac ctgggtgaga aaccgaacca   8940
caaacatctg atagagaggg actgcgcaac catcaccaaa gataaggttt gttttctcaa   9000
gatgaagaga gggtgtgcat ttacttatga cttatccctt cacaacctta cccggctgat   9060
cgaattggta cacaagaata acttggaaga caaagagatt cctgccgtta cggtcacaac   9120
ctggctggct tacacatttg taaatgaaga tatagggacc ataaaaccag ccttcgggga   9180
gaaaataaca ccagagatgc aggaggagat aaccttgcag cctgctgtag tggtggatgc   9240
aactgacgtg accgtgaccg tggtagggga aacccctact atgactacag gggagacccc   9300
aacaacgttc accagctcag gtccagaccc gaaaggccaa caagttttaa aactgggagt   9360
aggtgaaggc caataccccg ggactaatcc acagagagca agcctgcacg aagccataca   9420
aagcgcagat gaaaggccct ctgtgttgat attggggtct gataaagcca cctctaatag   9480
agtgaaaact gtaaagaatg tgaaggtata cagaggcagg gacccactag aagtgagaga   9540
tatgatgagg aggggaaaga tcctagtcat agccctgtct agggttgata atgctctatt   9600
gaaatttgta gattacaaag gcacctttct aactagagag accctggagg cattaagttt   9660
gggtaggcca aaaaagaaaa acataaccaa ggcagaagca cagtggttgc tgcgcctcga   9720
agaccaaatg gaagagctac ccgattggtt cgcagccggg gaacccattt ttttagaggc   9780
caatattaaa catgacaggt atcatctggt aggggatata gctactatca aagagaaagc   9840
caaacaattg gggggctacag actctacaaa gatatccaag gaggttggtg caaaagtata   9900
ttctatgaaa ttgagtaatt gggtgatgca agaagaaaac aaacagagca acttgacccc   9960
cttatttgaa gagctcctac agcagtgtcc acccggaggc caaaacaaaa ctgcacatat  10020
ggtctctgct taccaactag ctcaagggaa ctggatgcca accagctgcc atgtttttat  10080
ggggaccata tctgccagaa ggactaagac ccatccatat gaagcatatg tcaagttaag  10140
ggagttggta gaggaacaca agatgaaaac attgtgtccc ggatcaagtc tgcgtaagca  10200
caatgaatgg gtaattggca agatcaaata ccagggcaac ctgaggacca aacacatgtt  10260
gaaccccggc aaggtggcag agcaactgca cagagaagga cacagacaca atgtgtataa  10320
caagacaata ggctcagtga tgacagctac tggcatcagg ttggagaagt tgcccgtggt  10380
tagggcccag acagacacaa ccaacttcca ccaagcaata agggataaga tagacaagga  10440
agagaatcta cagaccccgg gtttacataa gaaactaatg gaagttttca atgcattgaa  10500
acgacccgag ttagagtcct cctatgacgc tgtggaatgg gaggaattgg agagaggaat  10560
aaacagaaag ggtgctgctg gtttctttga acgcaaaaac atagggggaga tattggattc  10620
agagaaaaat aaagtagaag agattattga caatctgaaa aagggtagaa atatcaaata  10680
ctatgaaacc gcaatcccaa aaaatgaaaa gagggatgtc aatgatgact ggaccgcagg  10740
```

-continued

```
tgactttgtg gacgagaaga aacccagagt catacaatac cctgaagcaa aaacaaggct  10800
ggccatcacc aaggtgatgt ataagtgggt gaagcagaag ccagtagtca tacccgggta  10860
tgaagggaag acacctctgt tccaaatttt tgacaaagta aagaaggaat gggatcaatt  10920
ccaaaatcca gtggcagtga gcttcgacac taaggcgtgg gacacccagg tgaccacaaa  10980
tgatctggag ctgataaagg acatacaaaa gtactacttc aagaagaaat ggcataaatt  11040
tattgacacc ctgactatgc atatgtcaga agtacccgta atcactgctg atggggaggt  11100
gtatataagg aaagggcaaa gaggtagtgg acagcccgac acaagcgcag gcaacagcat  11160
gctaaatgtg ttaacaatgg tttatgcctt ctgcgaggcc acaggggtac cctacaagag  11220
ttttgacagg gtggcaaaaa ttcatgtgtg cggggacgat ggtttcctga tcacagagag  11280
agctctcggc gagaaattcg caagcaaggg agtccaaatc ctgtatgaag ctgggaagcc  11340
ccagaagatc actgaagggg acaaaatgaa agtggcctac caatttgatg atattgagtt  11400
ttgctcccat acaccaatac aagtaaggtg gtcagataac acttctagct acatgccagg  11460
gagaaataca accacaatcc tggctaaaat ggccacaagg ttagattcca gtggtgagag  11520
gggtaccata gcgtacgaga aagcagtagc attcagcttc ctgctaatgt attcctggaa  11580
cccactaatc agaaggattt gcttattggt actatcaact gaactgcaag tgaaaccagg  11640
gaagtcaacc acttactatt atgaagggga cccgatatct gcctacaagg aagtcatcgg  11700
ccacaatctt ttcgatctca agagaacaag cttcgagaag ctggccaagt taaatctcag  11760
catgtccgta ctcggggcct ggactagaca caccagcaaa agactactac aagactgtgt  11820
caatatgggt gttaaagagg gcaactggtt agtcaatgca gacagactgg tgagtagtaa  11880
gactggaaat aggtatgtac ctggagaagg ccacaccctg caagggagac attatgaaga  11940
actggtgttg gcaagaaaac agatcaacag cttccaaggg acagacaggt acaatctagg  12000
cccaatagtc aacatggtgt taaggaggct gagagtcatg atgatgaccc tgatagggag  12060
aggggtatga gtgcgggtga cccgcgatct ggacccgtca gtaggaccct attgtagata  12120
acactaattt tttatttatt tagatattac tatttattta tttatttatt tattgaatga  12180
gtaagaactg gtacaaacta cctcatgtta ccacactaca ctcattttaa cagcacttta  12240
gctggaagga aaattcctga cgtccacagt tggactaagg taatttccta acggccc     12297
```

<210> SEQ ID NO 2
<211> LENGTH: 12297
<212> TYPE: DNA
<213> ORGANISM: Classical Swine Fever Virus

<400> SEQUENCE: 2

```
gtatacgagg ttagttcatt ctcgtgtaca tgattggaca aatcaaaatc tcaatttggt     60
tcagggcctc cctccagcga cggccgagct gggctagcca tgcccacagt aggactagca    120
aacggaggga ctagccgtag tggcgagctc cctgggtggt ctaagtcctg agtacaggac    180
agtcgtcagt agttcgacgt gagcagaagc ccacctcgag atgctatgtg gacgagggca    240
tgcccaagac acaccttaac cctagcgggg gtcgttaggg tgaaatcaca ccatgtgatg    300
ggagtacgac ctgatagggt gctgcagagg cccactatta ggctagtata aaaatctctg    360
ctgtacatgg cacatggagt tgaatcattt tgaactttta tacaaaacaa acaaacaaaa    420
accaatggga gtggaggaac cggtatacga tgtaacgggg agaccattgt ttggagaccc    480
aagtgaggta cacccacaat caacattgaa gctaccacat gataggggga gaggcaacat    540
caaaacaaca ctgaagaacc tacctaggag aggtgactgc aggagtggca accacctagg    600
```

-continued

```
cccggttagt gggatatatg taaagcccgg ccctgtcttt tatcaggact acatgggccc    660
agtctatcat agagcccctc tagagttttt tgacgaagca cagttttgtg aggtgaccaa    720
aaggataggt agggtgacag gtagtgacgg aaagctttac catatatacg tgtgcatcga    780
tggttgcatc ctgctgaagc tagccaagag gggcgagcca agaaccctga agtggattag    840
aaatctcacc gactgtccat tgtgggttac cagttgttct gatgatggtg caagtgcaag    900
taaagagaag aaaccagata ggatcaacaa gggtaaatta aagatagccc caaaagagca    960
tgagaaggac agcaggacta agccacctga tgctacgatt gtagtggaag gagtaaaata   1020
ccaggtcaaa aagaaaggta aagttaaggg aaagaatacc caagacggcc tgtaccacaa   1080
caagaataaa ccaccagaat ctaggaagaa attagaaaaa gccctattgg catgggcagt   1140
gatagcaatt atgttatacc aacctgttgc agccgaaaat ataactcaat ggaacctgag   1200
tgacaacggt accaatggta tccagcacgc tatgtacctt agaggagtca gcagaagctt   1260
gcatgggatc tggccagaaa aaatatgcaa aggagtcccc acctacctgg ccacagacac   1320
ggaactgaga gaaatacagg gaatgatgga tgccagcgag gggacaaact atacgtgctg   1380
taagttacag agacatgaat ggaacaaaca tggatggtgt aactggtata acatagaccc   1440
ctggatacag ttgatgaata gaacccaagc aaacttggca gaaggccctc cgagcaagga   1500
gtgcgccgtg acttgcaggt acgataaaaa tgctgacatt aacgtggtca cccaggccag   1560
aaacaggcca accaccctaa ctggctgcaa gaaagggaaa aatttttctt ttgcgggtac   1620
agttatagag ggcccatgta atttcaacgt ttctgttgag gatatcttat atggggatca   1680
tgagtgtggc agtctactcc aggatacggc tctataccta gtagatggaa tgaccaacac   1740
tatagagaga gccaggcagg gagccgcgag ggtgacatct tggctaggga ggcaactcag   1800
aactgccggg aagaggttgg agggcagaag caaaacctgg tttggtgcct atgccctatc   1860
accttattgt aatgtgacaa gcaaaatagg gtacatatgg tacactaaca actgtacccc   1920
ggcttgcctc cccaaaaata caaagataat aggccccggt aaatttgaca ctaacgcgga   1980
agacggaaag attctccatg agatgggggg ccacctatca gaatttctgc tgctctctct   2040
ggtcgttctg tctgacttcg cccctgaaac agccagcgcg ttatacctca ttttgcacta   2100
cgtgatccct caatcccatg aagaacctga aggctgtgac acaaaccagc tgaatttaac   2160
agtggaactc aggactgaag acgtgatacc atcatcagtc tggaatgttg gcaaatatgt   2220
gtgtgttaga ccagactggt ggccatatga aaccaaggtg gctttgttat ttgaagaggc   2280
aggacaggtc gtaaagttag ccttgcgggc actgagggat ttaaccaggg tctggaatag   2340
cgcatcaacc acggcattcc tcatctgctt gataaaagta ttaagaggac aggtcgtgca   2400
aggtgtgata tggctgttac tggtaactgg ggcacaaggc cggctagcct gcaaggaaga   2460
tcacaggtac gctatatcaa caaccaatga gatagggcta cttggggccg aaggtctcac   2520
taccacctgg aaagaataca accacaattt gcaactggat gatgggaccg tcaaggccat   2580
ctgcatggca ggttccttta aagtcacagc acttaatgtg gttagtagga ggtatctggc   2640
atcattacat aaggacgctt tacccacttc cgtgacattc gagctcctgt tcgacgggac   2700
cagcccattg accgaggaaa tgggagatga cttcgggttc ggactgtgtc cgtatgatac   2760
gagccctgta gtcaagggaa agtacgccac aaccttgttg aatggtagtg cattctacct   2820
agtttgccca atagggtgga cgggtgttat agagtgcacg gcagtgagcc cgacaactct   2880
gagaacagaa gtggtaaaga ccttcagaag agagaaaccc tttccgtaca gaagggattg   2940
```

-continued

```
tgtgaccact acagtggaaa atgaagatct attctactgt aaatgggggg gcaattggac   3000
atgtgtgaaa ggtgaaccag tgacctacac ggggggggcca gtaaaacaat gcagatggtg   3060
tggcttcgac ttcaatgagc ctgacggact cccacactac cccataggta agtgcatttt   3120
ggcaaatgag acaggttaca gaatagtgga ttcaacggac tgtaacagag atggcgttgt   3180
aatcagcaca gaggggagtc atgagtgctt gattggtaac acaactgtca aggtgcatgc   3240
attagatgaa agactaggcc ctatgccatg caggcctaag gagatcgtct ctagtgcggg   3300
acctgtaagg aaaacttcct gtacattcaa ctacgcaaaa actctgagga acaggtatta   3360
tgagcccagg gacagctatt tccaacaata tatgctcaag ggcgagtatc agtactggtt   3420
tgatctggat gtgaccgacc gccactcaga ttacttcgca gaattcattg tcttggtggt   3480
ggtggcactg ttgggaggaa gatatgtcct gtggctaata gtgacctaca tagttctaac   3540
agaacaactc gccgctggtc tacagttagg ccagggtgag gtagtgttaa tagggaactt   3600
aatcacccac acagatattg aggttgtagt atatttctta ctgctctatt tggtcatgag   3660
agatgagcct ataaagaaat ggatactact gctgttccat gctatgacca acaatccagt   3720
taagaccata acagtggcac tgctcatggt tagcggggtt gccaagggtg gaaagataga   3780
tggtggttgg cagcggctgc cggagaccaa ctttgatatc caactcgcgc tgacagttat   3840
agtagtcgct gtgatgttgc tggcaaagaa agatccgact accgtcccct tggttataac   3900
ggtggcaacc ctgagaacgg ctaagataac taatggactt agtacagatc tagccatagc   3960
tacagtgtca acagctttgc taacctggac ctacattagt gactattata aatacaagac   4020
cttgctacag taccttatta gcacagtgac aggtatcttc ttgataaggg tactgaaggg   4080
ggtaggtgag ttagatttac acaccccaac cttaccatct tacagacccc tcttcttcat   4140
cctcgtgtac ctcatttcca ctgcagtggt aacaagatgg aatctggaca tagccggatt   4200
gctgctgcag tgtgtcccaa ccctttttaat ggttttcacg atgtgggcag acatccttac   4260
cctgatcctc atactgccta cttacgagtt gacaaaacta tattacctca aggaagtgaa   4320
gattggggca gaaaggggct ggttgtggaa gaccaacttc aagagggtaa atgacatata   4380
cgaagttgac caagctggtg agggggtgta ccttttccca tcaaaacaaa agacaggtac   4440
aataacaggt actatgttgc cattgatcaa agccatactc ataagttgca tcagcaataa   4500
gtggcaattt atatatctat tgtacttgat attcgaagtg tcttactacc ttcacaagaa   4560
gatcatagat gaaatagcag gagggaccaa cttcatctcg agacttgtag ccgctctgat   4620
tgaagccaat tgggcctttg acaacgaaga agttagaggt ttaaagaagt tcttcctgct   4680
gtctagtagg gttaaagaac tgatcatcaa acacaaagtg aggaatgaag tgatggtcca   4740
ctggtttggc gacgaagagg tctatgggat gccgaagctg gttggcttag tcaaggcagc   4800
aacactgagt aaaaataaac attgtatttt gtgcaccgtc tgtgaaaaca gagagtggag   4860
aggagaaacc tgcccaaaat gcggccgttt tgggccacca gtgacctgtg gcatgaccct   4920
agccgacttt gaagaaaaac actataagag gattttcttt agagaggatc aatcagaagg   4980
gccggttagg gaggagtatg cagggtatct gcaatataga gccagagggc aattattcct   5040
gaggaatctc ccggtgctag caacaaaagt caagatgctc ctggtcggaa atcttgggac   5100
ggaggtgggg gatttggaac accttggctg ggtgctcaga gggcctgccg tttgcaagaa   5160
ggttaccgaa catgagaaat gcaccacatc cataatggac aaattaactg ctttcttcgg   5220
tgttatgcca aggggcacca cacctagagc ccctgtgaga ttccccacct ctctcttaaa   5280
gataagaagg gggctggaaa ctggctgggc gtacacacac caaggtggca tcagttcagt   5340
```

```
ggaccatgtc acttgtggga aagacttact ggtatgtgac actatgggcc ggacaagggt   5400
tgtttgccaa tcaaataaca agatgacaga cgagtccgag tatggagtta aaactgactc   5460
cggatgcccg gagggagcta ggtgttacgt gttcaaccca gaggcagtta acatatccgg   5520
gactaaagga gccatggtcc acttacaaaa aactggagga gaattcacct gtgtgacagc   5580
atcagggact ccggccttct ttgatctcaa gaacctcaaa ggctggtcag ggctgccgat   5640
atttgaggca tcaagtggaa gagtagtcgg cagggttaag gtcgggaaga atgaggactc   5700
taaaccaacc aagcttatga gtggaataca aacagtctcc aaaagtacca cagacttgac   5760
agaaatggta aagaaaataa caaccatgaa caggggagaa ttcagacaaa taacccttgc   5820
cacaggtgcc ggaaaaacca cggaactccc tagatcagtc atagaagaga taggaaggca   5880
taagagggtc ttggtcttga tccctctgag ggcggcagca gagtcagtat accaatatat   5940
gagacaaaaa cacccaagca tagcattcaa cttgaggata ggggagatga aggaagggga   6000
catggccaca gggataacct atgcctcata tggttacttc tgtcagatgc cacaacctaa   6060
gctgcgagcc gcgatggttg agtactcctt catattcctt gatgagtacc actgtgccac   6120
ccccgaacaa ttggctatca tgggaaagat ccacagattt tcagagaacc tgcgggtagt   6180
agccatgacc gcaacaccag caggcacggt aacaactaca gggcaaaaac accctataga   6240
agaatacata gccccagaag tgatgaaggg ggaagactta ggttcagagt acttggacat   6300
agctggacta aagataccag tagaggagat gaagagtaac atgctggtct ttgtgcccac   6360
aaggaacatg gctgtagaga cggcaaagaa actgaaagct aagggttata actcaggcta   6420
ctattatagt ggagaggatc catctaacct gagggtggta acatcacagt ccccgtacgt   6480
ggtggtagca accaacgcaa tagaatcagg tgttactctc ccagacttgg atgtggtcgt   6540
cgacacaggg cttaagtgtg aaaagaggat acggctgtca cctaagatgc ccttcatagt   6600
gacgggcctg aagagaatgg ctgtcacgat tggggaacaa gcccagagaa gggggagagt   6660
tgggagagtg aagcctggga gatactacag gagtcaagaa acccccgttg gttccaaaga   6720
ttaccattac gacctactgc aagcacagag gtacggtata gaagatggga taaacatcac   6780
caaatctttt agagagatga attatgattg gagcctttat gaggaggata gtctgatgat   6840
tacacaattg gaaatcctca acaatctgtt gatatcagaa gagctaccaa tggcagtaaa   6900
aaatataatg gccaggactg accacccaga accaatccaa ctggcgtaca acagctacga   6960
aacgcaggtg ccagtgctat tcccaaaaat aaaaaatgga gaggtgactg acagttacga   7020
taactatacc ttcctcaacg caagaaagct gggggatgat gtacctccct acgtgtatgc   7080
cacagaggat gaggacttag cggtagagct gctgggctta gactggccgg accctgggaa   7140
ccaaggaacc gtggaggctg gtagagcact aaaacaagta gttggtctat caacagctga   7200
gaacgccctg ttagtagctt tattcggcta tgtaggatat caggcactct caaagaggca   7260
tataccagta gtcacagaca tatattcaat tgaagatcac aggttggaag acaccacaca   7320
cctacagtat gccccgaatg ctatcaagac ggaggggaag gagacagaat tgaaggagct   7380
agctcagggg gatgtgcaga gatgtatgga agctatgact aattatgcaa gagatggcat   7440
ccaattcatg aagtctcagg cactgaaagt gaaagaaacc cccacttaca aagagacaat   7500
ggacaccgtg gcggactatg taaagaagtt catggaggca ctggcggaca gcaaagaaga   7560
catcataaaa tatgggttgt gggggacgca cacaacctta tataagagca tcggtgctag   7620
gcttgggaac gagactgcgt tcgctaccct ggtcgtgaaa tggctggcat ttgggggaga   7680
```

-continued atcaatagca gaccatgtca aacaagcggc cacagacttg gtcgtttact atatcatcaa 7740
cagacctcag ttcccaggag acacggagac acaacaggaa ggaaggaaat ttgtagccag 7800
cctactggtc tcagccctgg ctacttacac ttacaaaagc tggaattaca ataatctgtc 7860
caagatagtt gaaccggctt tggctactct gccctatgcc gccacagctc tcaagctatt 7920
cgcccccact cgattggaga gcgttgtcat actgagtacc gcaatctaca aaacctacct 7980
atcaatcagg cgcggaaaaa gcgatggttt gctaggcaca ggggttagtg cggctatgga 8040
aatcatgtca caaaacccag tatctgtggg tatagcggtc atgctagggg tgggggccgt 8100
agcggcccac aatgcaatcg aagccagtga gcagaagaga acactactca tgaaagtttt 8160
tgtaaagaac ttcttggatc aggcagccac tgatgaatta gtcaaggaga gccctgagaa 8220
aataataatg gctttgtttg aagcagtgca gacagtcggc aaccctctta gactggtata 8280
ccacctttac ggagtttttt acaaagggtg ggaggcaaaa gagttggccc aaaggacagc 8340
cggtaggaat cttttcactt tgataatgtt tgaggctgtg gaactactgg gagtagatag 8400
cgaaggaaag atccgccagc tatcaagcaa ttacatacta gagctcctgt ataagttccg 8460
tgacagtatc aagtccagcg tgaggcagat ggcaatcagc tgggcccctg cccctttag 8520
ttgtgattgg acaccgacgg atgacagaat agggcttccc caagataatt tcctccgagt 8580
ggagacaaaa tgcccctgtg gttacaagat gaaagcagtt aagaattgtg ctggggagtt 8640
gagactctta gaagaggaag gctcatttct ctgcaggaat aaattcggga gaggttcacg 8700
gaactacagg gtgacaaaat actatgatga caatctatca gaaataaagc cagtgataag 8760
aatggaagga catgtggaac tctactacaa gggagccact attaaactgg atttcaacaa 8820
cagtaaaaca atattggcaa ccgataaatg ggaggtcgat cactccactc tggtcagggt 8880
gctcaagagg cacacagggg ctggatatcg tggggcatac ctgggtgaga aaccgaacca 8940
caaacatctg atagagaggg actgcgcaac catcaccaaa gataaggttt gttttctcaa 9000
gatgaagaga gggtgtgcat ttacttatga cttatccctt cacaacctta cccggctgat 9060
cgaattggta cacaagaata acttggaaga caaagagatt cctgccgtta cggtcacaac 9120
ctggctggct tacacatttg taaatgaaga tatagggacc ataaaaccag ccttcgggga 9180
gaaaataaca ccagagatgc aggaggagat aaccttgcag cctgctgtag tggtggatgc 9240
aactgacgtg accgtgaccg tggtagggga aacccctact atgactacag gggagacccc 9300
aacaacgttc accagctcag gtccagaccc gaaaggccaa caagttttaa aactgggagt 9360
aggtgaaggc caataccccg ggactaatcc acagagagca agcctgcacg aagccataca 9420
aagcgcagat gaaaggccct ctgtgttgat attggggtct gataaagcca cctctaatag 9480
agtgaaaact gtaaagaatg tgaaggtata cagaggcagg gacccactag aagtgagaga 9540
tatgatgagg aggggaaaga tcctagtcat agccctgtct agggttgata atgctctatt 9600
gaaatttgta gattacaaag gcacctttct aactagagag accctggagg cattaagttt 9660
gggtaggcca aaaaagaaaa acataaccaa ggcagaagca cagtggttgc tgcgcctcga 9720
agaccaaatg gaagagctac ccgattggtt cgcagccggg gaacccattt ttttagaggc 9780
caatattaaa catgacaggt atcatctggt aggggatata gctactatca aagagaaagc 9840
caaacaattg ggggctacag actctacaaa gatatccaag gaggttggtg caaaagtata 9900
ttctatgaaa ttgagtaatt gggtgatgca agaagaaaac aaacagagca acttgacccc 9960
cttatttgaa gagctcctac agcagtgtcc acccggaggc caaaacaaaa ctgcacatat 10020
ggtctctgct taccaactag ctcaagggaa ctggatgcca accagctgcc atgtttttat 10080

-continued

```
ggggaccata tctgccagaa ggactaagac ccatccatat gaagcatatg tcaagttaag  10140
ggagttggta gaggaacaca agatgaaaac attgtgtccc ggatcaagtc tgcgtaagca  10200
caatgaatgg gtaattggca agatcaaata ccagggcaac ctgaggacca aacacatgtt  10260
gaaccccggc aaggtggcag agcaactgca cagagaagga cacagacaca atgtgtataa  10320
caagacaata ggctcagtga tgacagctac tggcatcagg ttggagaagt tgcccgtggt  10380
tagggcccag acagacacaa ccaacttcca ccaagcaata agggataaga tagacaagga  10440
agagaatcta cagaccccgg gtttacataa gaaactaatg gaagttttca atgcattgaa  10500
acgacccgag ttagagtcct cctatgacgc tgtggaatgg gaggaattgg agagaggaat  10560
aaacagaaag ggtgctgctg gtttctttga acgcaaaaac ataggggaga tattggattc  10620
agagaaaaat aaagtagaag agattattga caatctgaaa aagggtagaa atatcaaata  10680
ctatgaaacc gcaatcccaa aaaatgaaaa gagggatgtc aatgatgact ggaccgcagg  10740
tgactttgtg gacgagaaga aacccagagt catacaatac cctgaagcaa aaacaaggct  10800
ggccatcacc aaggtgatgt ataagtgggt gaagcagaag ccagtagtca tacccgggta  10860
tgaagggaag acacctctgt tccaaatttt tgacaaagta aagaaggaat gggatcaatt  10920
ccaaaatcca gtggcagtga gcttcgacac taaggcgtgg gacacccagg tgaccacaaa  10980
tgatctggag ctgataaagg acatacaaaa gtactacttc aagaagaaat ggcataaatt  11040
tattgacacc ctgactatgc atatgtcaga agtacccgta atcactgctg atggggaggt  11100
gtatataagg aaagggcaaa gaggtagtgg acagcccgac acaagcgcag gcaacagcat  11160
gctaaatgtg ttaacaatgg tttatgcctt ctgcgaggcc acaggggtac cctacaagag  11220
ttttgacagg gtggcaaaaa ttcatgtgtg cggggacgat ggtttcctga tcacagagag  11280
agctctcggc gagaaattcg caagcaaggg agtccaaatc ctgtatgaag ctgggaagcc  11340
ccagaagatc actgaagggg acaaaatgaa agtggcctac caatttgatg atattgagtt  11400
ttgctcccat acaccaatac aagtaaggtg gtcagataac acttctagct acatgccagg  11460
gagaaataca accacaatcc tggctaaaat ggccacaagg ttagattcca gtggtgagag  11520
gggtaccata gcgtacgaga aagcagtagc attcagcttc ctgctaatgt attcctggaa  11580
cccactaatc agaaggattt gcttattggt actatcaact gaactgcaag tgaaaccagg  11640
gaagtcaacc acttactatt atgaagggga cccgatatct gcctacaagg aagtcatcgg  11700
ccacaatctt ttcgatctca agagaacaag cttcgagaag ctggccaagt taaatctcag  11760
catgtccgta ctcggggcct ggactagaca caccagcaaa agactactac aagactgtgt  11820
caatatgggt gttaaagagg gcaactggtt agtcaatgca gacagactgg tgagtagtaa  11880
gactggaaat aggtatgtac ctggagaagg ccacaccctg caagggagac attatgaaga  11940
actggtgttg gcaagaaaac agatcaacag cttccaaggg acagacaggt acaatctagg  12000
cccaatagtc aacatggtgt taaggaggct gagagtcatg atgatgaccc tgatagggag  12060
aggggtatga gtgcgggtga cccgcgatct ggacccgtca gtaggaccct attgtagata  12120
acactaattt tttatttatt tagatattac tatttattta tttatttatt tattgaatga  12180
gtaagaactg gtacaaacta cctcatgtta ccacactaca ctcattttaa cagcacttta  12240
gctggaagga aaattcctga cgtccacagt tggactaagg taatttccta acggccc     12297
```

<210> SEQ ID NO 3
<211> LENGTH: 12297
<212> TYPE: DNA

<213> ORGANISM: Classical Swine Fever Virus

<400> SEQUENCE: 3

```
gtatacgagg ttagttcatt ctcgtgtaca tgattggaca aatcaaaatc tcaatttggt     60
tcagggcctc cctccagcga cggccgagct gggctagcca tgcccacagt aggactagca    120
aacggaggga ctagccgtag tggcgagctc cctgggtggt ctaagtcctg agtacaggac    180
agtcgtcagt agttcgacgt gagcagaagc ccacctcgag atgctatgtg gacgagggca    240
tgcccaagac acaccttaac cctagcgggg gtcgttaggg tgaaatcaca ccatgtgatg    300
ggagtacgac ctgatagggt gctgcagagg cccactatta ggctagtata aaaatctctg    360
ctgtacatgg cacatggagt tgaatcattt tgaactttta tacaaaacaa acaaacaaaa    420
accaatggga gtggaggaac cggtatacga tgtaacgggg agaccattgt ttggagaccc    480
aagtgaggta cacccacaat caacattgaa gctaccacat gataggggga gaggcaacat    540
caaaacaaca ctgaagaacc tacctaggag aggtgactgc aggagtggca accacctagg    600
cccggttagt gggatatatg taaagcccgg ccctgtcttt tatcaggact acatgggccc    660
agtctatcat agagcccctc tagagttttt tgacgaagca cagttttgtg aggtgaccaa    720
aaggataggt agggtgacag gtagtgacgg aaagctttac catatatacg tgtgcatcga    780
tggttgcatc ctgctgaagc tagccaagag gggcgagcca agaaccctga agtggattag    840
aaatctcacc gactgtccat tgtgggttac cagttgttct gatgatggtg caagtgcaag    900
taaagagaag aaaccagata ggatcaacaa gggtaaatta aagatagccc caaaagagca    960
tgagaaggac agcaggacta agccacctga tgctacgatt gtagtggaag gagtaaaata   1020
ccaggtcaaa aagaaaggta aagttaaggg aaagaatacc caagacggcc tgtaccacaa   1080
caagaataaa ccaccagaat ctaggaagaa attagaaaaa gccctattgg catgggcagt   1140
gatagcaatt atgttatacc aacctgttgc agccgaagct ataactcaat ggaacctgag   1200
tgacaacggt accaatggta tccagcacgc tatgtacctt agaggagtca gcagaagctt   1260
gcatgggatc tggccagaaa aaatatgcaa aggagtcccc acctacctgg ccacagacac   1320
ggaactgaga gaaatacagg gaatgatgga tgccagcgag gggacaaact atacgtgctg   1380
taagttacag agacatgaat ggaacaaaca tggatggtgt aactggtata acatagaccc   1440
ctggatacag ttgatgaata gaacccaagc aaacttggca gaaggccctc cgagcaagga   1500
gtgcgccgtg acttgcaggt acgataaaaa tgctgacatt aacgtggtca cccaggccag   1560
aaacaggcca accaccctaa ctggctgcaa gaaagggaaa aatttttctt ttgcgggtac   1620
agttatagag ggcccatgta atttcaacgt ttctgttgag gatatcttat atggggatca   1680
tgagtgtggc agtctactcc aggatacggc tctataccta gtagatggaa tgaccaacac   1740
tatagagaga gccaggcagg gagccgcgag ggtgacatct tggctaggga ggcaactcag   1800
aactgccggg aagaggttgg agggcagaag caaaacctgg tttggtgcct atgccctatc   1860
accttattgt aatgtgacaa gcaaaatagg gtacatatgg tacactaaca actgtacccc   1920
ggcttgcctc cccaaaaata caaagataat aggccccggt aaatttgaca ctaacgcgga   1980
agacggaaag attctccatg agatgggggg ccacctatca gaatttctgc tgctctctct   2040
ggtcgttctg tctgacttcg cccctgaaac agccagcgcg ttatacctca ttttgcacta   2100
cgtgatccct caatcccatg aagaacctga aggctgtgac acaaaccagc tgaatttaac   2160
agtggaactc aggactgaag acgtgatacc atcatcagtc tggaatgttg gcaaatatgt   2220
gtgtgttaga ccagactggt ggccatatga aaccaaggtg gctttgttat ttgaagaggc   2280
```

-continued

```
aggacaggtc gtaaagttag ccttgcgggc actgagggat ttaaccaggg tctggaatag   2340
cgcatcaacc acggcattcc tcatctgctt gataaaagta ttaagaggac aggtcgtgca   2400
aggtgtgata tggctgttac tggtaactgg ggcacaaggc cggctagcct gcaaggaaga   2460
tcacaggtac gctatatcaa caaccaatga gatagggcta cttggggccg aaggtctcac   2520
taccacctgg aaagaataca accacaattt gcaactggat gatgggaccg tcaaggccat   2580
ctgcatggca ggttccttta aagtcacagc acttaatgtg gttagtagga ggtatctggc   2640
atcattacat aaggacgctt tacccacttc cgtgacattc gagctcctgt tcgacgggac   2700
cagcccattg accgaggaaa tgggagatga cttcgggttc ggactgtgtc cgtatgatac   2760
gagccctgta gtcaagggaa agtacgccac aaccttgttg aatggtagtg cattctacct   2820
agtttgccca atagggtgga cgggtgttat agagtgcacg gcagtgagcc cgacaactct   2880
gagaacagaa gtggtaaaga ccttcagaag agagaaaccc tttccgtaca gaagggattg   2940
tgtgaccact acagtggaaa atgaagatct attctactgt aaatgggggg gcaattggac   3000
atgtgtgaaa ggtgaaccag tgacctacac ggggggggcca gtaaaacaat gcagatggtg   3060
tggcttcgac ttcaatgagc ctgacggact cccacactac cccataggta agtgcatttt   3120
ggcaaatgag acaggttaca gaatagtgga ttcaacggac tgtaacagag atggcgttgt   3180
aatcagcaca gaggggagtc atgagtgctt gattggtaac acaactgtca aggtgcatgc   3240
attagatgaa agactaggcc ctatgccatg caggcctaag gagatcgtct ctagtgcggg   3300
acctgtaagg aaaacttcct gtacattcaa ctacgcaaaa actctgagga acaggtatta   3360
tgagcccagg gacagctatt tccaacaata tatgctcaag ggcgagtatc agtactggtt   3420
tgatctggat gtgaccgacc gccactcaga ttacttcgca gaattcattg tcttggtggt   3480
ggtggcactg ttgggaggaa gatatgtcct gtggctaata gtgacctaca tagttctaac   3540
agaacaactc gccgctggtc tacagttagg ccagggtgag gtagtgttaa tagggaactt   3600
aatcacccac acagatattg aggttgtagt atatttctta ctgctctatt tggtcatgag   3660
agatgagcct ataaagaaat ggatactact gctgttccat gctatgacca acaatccagt   3720
taagaccata acagtggcac tgctcatggt tagcggggtt gccaagggtg gaaagataga   3780
tggtggttgg cagcggctgc cggagaccaa ctttgatatc caactcgcgc tgacagttat   3840
agtagtcgct gtgatgttgc tggcaaagaa agatccgact accgtcccct tggttataac   3900
ggtggcaacc ctgagaacgg ctaagataac taatggactt agtacagatc tagccatagc   3960
tacagtgtca acagctttgc taacctggac ctacattagt gactattata aatacaagac   4020
cttgctacag taccttatta gcacagtgac aggtatcttc ttgataaggg tactgaaggg   4080
ggtaggtgag ttagatttac acaccccaac cttaccatct tacagacccc tcttcttcat   4140
cctcgtgtac ctcatttcca ctgcagtggt aacaagatgg aatctggaca tagccggatt   4200
gctgctgcag tgtgtcccaa cccttttaat ggttttcacg atgtgggcag acatccttac   4260
cctgatcctc atactgccta cttacgagtt gacaaaacta tattacctca aggaagtgaa   4320
gattggggca gaaaggggct ggttgtggaa gaccaacttc aagagggtaa atgacatata   4380
cgaagttgac caagctggtg aggggggtgta cctttttccca tcaaaacaaa agacaggtac   4440
aataacaggt actatgttgc cattgatcaa agccatactc ataagttgca tcagcaataa   4500
gtggcaattt atatatctat tgtacttgat attcgaagtg tcttactacc ttcacaagaa   4560
gatcatagat gaaatagcag gagggaccaa cttcatctcg agacttgtag ccgctctgat   4620
```

```
tgaagccaat tgggcctttg acaacgaaga agttagaggt ttaaagaagt tcttcctgct   4680
gtctagtagg gttaaagaac tgatcatcaa acacaaagtg aggaatgaag tgatggtcca   4740
ctggtttggc gacgaagagg tctatgggat gccgaagctg gttggcttag tcaaggcagc   4800
aacactgagt aaaaataaac attgtatttt gtgcaccgtc tgtgaaaaca gagagtggag   4860
aggagaaacc tgcccaaaat gcggccgttt tgggccacca gtgacctgtg gcatgaccct   4920
agccgacttt gaagaaaaac actataagag gattttcttt agagaggatc aatcagaagg   4980
gccggttagg gaggagtatg cagggtatct gcaatataga gccagagggc aattattcct   5040
gaggaatctc ccggtgctag caacaaaagt caagatgctc ctggtcggaa atcttgggac   5100
ggaggtgggg gatttggaac accttggctg ggtgctcaga gggcctgccg tttgcaagaa   5160
ggttaccgaa catgagaaat gcaccacatc cataatggac aaattaactg ctttcttcgg   5220
tgttatgcca aggggcacca cacctagagc ccctgtgaga ttccccacct ctctcttaaa   5280
gataagaagg gggctggaaa ctggctgggc gtacacacac caaggtggca tcagttcagt   5340
ggaccatgtc acttgtggga aagacttact ggtatgtgac actatgggcc ggacaagggt   5400
tgtttgccaa tcaaataaca agatgacaga cgagtccgag tatggagtta aaactgactc   5460
cggatgcccg gagggagcta ggtgttacgt gttcaaccca gaggcagtta acatatccgg   5520
gactaaagga gccatggtcc acttacaaaa aactggagga gaattcacct gtgtgacagc   5580
atcagggact ccggccttct ttgatctcaa gaacctcaaa ggctggtcag ggctgccgat   5640
atttgaggca tcaagtggaa gagtagtcgg cagggttaag gtcgggaaga atgaggactc   5700
taaaccaacc aagcttatga gtggaataca aacagtctcc aaaagtacca cagacttgac   5760
agaaatggta aagaaaataa caaccatgaa caggggagaa ttcagacaaa taacccttgc   5820
cacaggtgcc ggaaaaacca cggaactccc tagatcagtc atagaagaga taggaaggca   5880
taagagggtc ttggtcttga tccctctgag ggcggcagca gagtcagtat accaatatat   5940
gagacaaaaa cacccaagca tagcattcaa cttgaggata ggggagatga aggaagggga   6000
catggccaca gggataacct atgcctcata tggttacttc tgtcagatgc cacaacctaa   6060
gctgcgagcc gcgatggttg agtactcctt catattcctt gatgagtacc actgtgccac   6120
ccccgaacaa ttggctatca tgggaaagat ccacagattt tcagagaacc tgcgggtagt   6180
agccatgacc gcaacaccag caggcacggt aacaactaca gggcaaaaac accctataga   6240
agaatacata gccccagaag tgatgaaggg ggaagactta ggttcagagt acttggacat   6300
agctggacta aagataccag tagaggagat gaagagtaac atgctggtct ttgtgcccac   6360
aaggaacatg gctgtagaga cggcaaagaa actgaaagct aagggttata actcaggcta   6420
ctattatagt ggagaggatc catctaacct gagggtggta acatcacagt ccccgtacgt   6480
ggtggtagca accaacgcaa tagaatcagg tgttactctc ccagacttgg atgtggtcgt   6540
cgacacaggg cttaagtgtg aaaagaggat acggctgtca cctaagatgc ccttcatagt   6600
gacgggcctg aagagaatgg ctgtcacgat tggggaacaa gcccagagaa gggggagagt   6660
tgggagagtg aagcctggga gatactacag gagtcaagaa acccccgttg gttccaaaga   6720
ttaccattac gacctactgc aagcacagag gtacggtata gaagatggga taaacatcac   6780
caaatctttt agagagatga attatgattg gagcctttat gaggaggata gtctgatgat   6840
tacacaattg gaaatcctca acaatctgtt gatatcagaa gagctaccaa tggcagtaaa   6900
aaatataatg gccaggactg accacccaga accaatccaa ctggcgtaca acagctacga   6960
aacgcaggtg ccagtgctat tcccaaaaat aaaaaatgga gaggtgactg acagttacga   7020
```

```
taactatacc ttcctcaacg caagaaagct gggggatgat gtacctccct acgtgtatgc   7080
cacagaggat gaggacttag cggtagagct gctgggctta gactggccgg accctgggaa   7140
ccaaggaacc gtggaggctg gtagagcact aaaacaagta gttggtctat caacagctga   7200
gaacgccctg ttagtagctt tattcggcta tgtaggatat caggcactct caaagaggca   7260
tataccagta gtcacagaca tatattcaat tgaagatcac aggttggaag acaccacaca   7320
cctacagtat gccccgaatg ctatcaagac ggaggggaag gagacagaat tgaaggagct   7380
agctcagggg gatgtgcaga gatgtatgga agctatgact aattatgcaa gagatggcat   7440
ccaattcatg aagtctcagg cactgaaagt gaaagaaacc cccacttaca aagagacaat   7500
ggacaccgtg gcggactatg taaagaagtt catggaggca ctggcggaca gcaaagaaga   7560
catcataaaa tatgggttgt gggggacgca cacaacctta tataagagca tcggtgctag   7620
gcttgggaac gagactgcgt tcgctaccct ggtcgtgaaa tggctggcat ttgggggaga   7680
atcaatagca gaccatgtca aacaagcggc cacagacttg gtcgtttact atatcatcaa   7740
cagacctcag ttcccaggag acacggagac acaacaggaa ggaaggaaat ttgtagccag   7800
cctactggtc tcagccctgg ctacttacac ttacaaaagc tggaattaca ataatctgtc   7860
caagatagtt gaaccggctt tggctactct gccctatgcc gccacagctc tcaagctatt   7920
cgcccccact cgattggaga gcgttgtcat actgagtacc gcaatctaca aaacctacct   7980
atcaatcagg cgcggaaaaa gcgatggttt gctaggcaca ggggttagtg cggctatgga   8040
aatcatgtca caaaacccag tatctgtggg tatagcggtc atgctagggg tgggggccgt   8100
agcggcccac aatgcaatcg aagccagtga gcagaagaga acactactca tgaaagtttt   8160
tgtaaagaac ttcttggatc aggcagccac tgatgaatta gtcaaggaga gccctgagaa   8220
aataataatg gctttgtttg aagcagtgca gacagtcggc aaccctctta gactggtata   8280
ccacctttac ggagtttttt acaaagggtg ggaggcaaaa gagttggccc aaaggacagc   8340
cggtaggaat cttttcactt tgataatgtt tgaggctgtg gaactactgg gagtagatag   8400
cgaaggaaag atccgccagc tatcaagcaa ttacatacta gagctcctgt ataagttccg   8460
tgacagtatc aagtccagcg tgaggcagat ggcaatcagc tgggcccctg ccccttttag   8520
ttgtgattgg acaccgacgg atgacagaat agggcttccc caagataatt tcctccgagt   8580
ggagacaaaa tgcccctgtg gttacaagat gaaagcagtt aagaattgtg ctggggagtt   8640
gagactctta gaagaggaag gctcatttct ctgcaggaat aaattcggga gaggttcacg   8700
gaactacagg gtgacaaaat actatgatga caatctatca gaaataaagc cagtgataag   8760
aatggaagga catgtggaac tctactacaa gggagccact attaaactgg atttcaacaa   8820
cagtaaaaca atattggcaa ccgataaatg ggaggtcgat cactccactc tggtcagggt   8880
gctcaagagg cacacagggg ctggatatcg tggggcatac ctgggtgaga aaccgaacca   8940
caaacatctg atagagaggg actgcgcaac catcaccaaa gataaggttt gttttctcaa   9000
gatgaagaga gggtgtgcat ttacttatga cttatccctt cacaacctta cccggctgat   9060
cgaattggta cacaagaata acttggaaga caaagagatt cctgccgtta cggtcacaac   9120
ctggctggct tacacatttg taaatgaaga tatagggacc ataaaaccag ccttcgggga   9180
gaaaataaca ccagagatgc aggaggagat aaccttgcag cctgctgtag tggtggatgc   9240
aactgacgtg accgtgaccg tggtagggga aacccctact atgactacag gggagacccc   9300
aacaacgttc accagctcag gtccagaccc gaaaggccaa caagttttaa aactgggagt   9360
```

-continued

```
aggtgaaggc caataccccg ggactaatcc acagagagca agcctgcacg aagccataca   9420
aagcgcagat gaaaggccct ctgtgttgat attggggtct gataaagcca cctctaatag   9480
agtgaaaact gtaaagaatg tgaaggtata cagaggcagg gacccactag aagtgagaga   9540
tatgatgagg aggggaaaga tcctagtcat agccctgtct agggttgata atgctctatt   9600
gaaatttgta gattacaaag gcacctttct aactagagag accctggagg cattaagttt   9660
gggtaggcca aaaaagaaaa acataaccaa ggcagaagca cagtggttgc tgcgcctcga   9720
agaccaaatg gaagagctac ccgattggtt cgcagccggg gaacccattt ttttagaggc   9780
caatattaaa catgacaggt atcatctggt aggggatata gctactatca aagagaaagc   9840
caaacaattg gggggctacag actctacaaa gatatccaag gaggttggtg caaaagtata   9900
ttctatgaaa ttgagtaatt gggtgatgca agaagaaaac aaacagagca acttgacccc   9960
cttatttgaa gagctcctac agcagtgtcc acccggaggc caaaacaaaa ctgcacatat  10020
ggtctctgct taccaactag ctcaagggaa ctggatgcca accagctgcc atgtttttat  10080
ggggaccata tctgccagaa ggactaagac ccatccatat gaagcatatg tcaagttaag  10140
ggagttggta gaggaacaca agatgaaaac attgtgtccc ggatcaagtc tgcgtaagca  10200
caatgaatgg gtaattggca agatcaaata ccagggcaac ctgaggacca aacacatgtt  10260
gaaccccggc aaggtggcag agcaactgca cagagaagga cacagacaca atgtgtataa  10320
caagacaata ggctcagtga tgacagctac tggcatcagg ttggagaagt tgcccgtggt  10380
tagggcccag acagacacaa ccaacttcca ccaagcaata agggataaga tagacaagga  10440
agagaatcta cagaccccgg gtttacataa gaaactaatg gaagttttca atgcattgaa  10500
acgacccgag ttagagtcct cctatgacgc tgtggaatgg gaggaattgg agagaggaat  10560
aaacagaaag ggtgctgctg gtttctttga acgcaaaaac ataggggaga tattggattc  10620
agagaaaaat aaagtagaag agattattga caatctgaaa aagggtagaa atatcaaata  10680
ctatgaaacc gcaatcccaa aaaatgaaaa gagggatgtc aatgatgact ggaccgcagg  10740
tgactttgtg gacgagaaga aacccagagt catacaatac cctgaagcaa aaacaaggct  10800
ggccatcacc aaggtgatgt ataagtgggt gaagcagaag ccagtagtca tacccgggta  10860
tgaagggaag acacctctgt tccaaatttt tgacaaagta aagaaggaat gggatcaatt  10920
ccaaaatcca gtggcagtga gcttcgacac taaggcgtgg gacacccagg tgaccacaaa  10980
tgatctggag ctgataaagg acatacaaaa gtactacttc aagaagaaat ggcataaatt  11040
tattgacacc ctgactatgc atatgtcaga agtacccgta atcactgctg atggggaggt  11100
gtatataagg aaagggcaaa gaggtagtgg acagcccgac acaagcgcag gcaacagcat  11160
gctaaatgtg ttaacaatgg tttatgcctt ctgcgaggcc acaggggtac cctacaagag  11220
ttttgacagg gtggcaaaaa ttcatgtgtg cggggacgat ggtttcctga tcacagagag  11280
agctctcggc gagaaattcg caagcaaggg agtccaaatc ctgtatgaag ctgggaagcc  11340
ccagaagatc actgaagggg acaaaatgaa agtggcctac caatttgatg atattgagtt  11400
ttgctcccat acaccaatac aagtaaggtg gtcagataac acttctagct acatgccagg  11460
gagaaataca accacaatcc tggctaaaat ggccacaagg ttagattcca gtggtgagag  11520
gggtaccata gcgtacgaga aagcagtagc attcagcttc ctgctaatgt attcctggaa  11580
cccactaatc agaaggattt gcttattggt actatcaact gaactgcaag tgaaaccagg  11640
gaagtcaacc acttactatt atgaagggga cccgatatct gcctacaagg aagtcatcgg  11700
ccacaatctt ttcgatctca agagaacaag cttcgagaag ctggccaagt taaatctcag  11760
```

```
catgtccgta ctcggggcct ggactagaca caccagcaaa agactactac aagactgtgt  11820

caatatgggt gttaaagagg gcaactggtt agtcaatgca gacagactgg tgagtagtaa  11880

gactggaaat aggtatgtac ctggagaagg ccacaccctg caagggagac attatgaaga  11940

actggtgttg gcaagaaaac agatcaacag cttccaaggg acagacaggt acaatctagg  12000

cccaatagtc aacatggtgt taaggaggct gagagtcatg atgatgaccc tgatagggag  12060

aggggtatga gtgcgggtga cccgcgatct ggacccgtca gtaggaccct attgtagata  12120

acactaattt tttatttatt tagatattac tatttattta tttatttatt tattgaatga  12180

gtaagaactg gtacaaacta cctcatgtta ccacactaca ctcattttaa cagcacttta  12240

gctggaagga aaattcctga cgtccacagt tggactaagg taatttccta acggccc     12297
```

```
<210> SEQ ID NO 4
<211> LENGTH: 45
<212> TYPE: DNA
<213> ORGANISM: Classical Swine Fever Virus

<400> SEQUENCE: 4

catcattaca taaggacgct ttagccactt ccgtgacatt cgagc                     45


<210> SEQ ID NO 5
<211> LENGTH: 45
<212> TYPE: DNA
<213> ORGANISM: Classical Swine Fever Virus

<400> SEQUENCE: 5

ccctgtagtc aagggaaagt acgccacaac cttgttgaat ggtag                     45


<210> SEQ ID NO 6
<211> LENGTH: 45
<212> TYPE: DNA
<213> ORGANISM: Classical Swine Fever Virus

<400> SEQUENCE: 6

aaagtacaac acaaccttgt tggctggtag tgcattctac ctagt                     45


<210> SEQ ID NO 7
<211> LENGTH: 45
<212> TYPE: DNA
<213> ORGANISM: Classical Swine Fever Virus

<400> SEQUENCE: 7

attctactgt aaatgggggg gcgcttggac atgtgtgaaa ggtga                     45


<210> SEQ ID NO 8
<211> LENGTH: 45
<212> TYPE: DNA
<213> ORGANISM: Classical Swine Fever Virus

<400> SEQUENCE: 8

ataggtaagt gcattttggc agctgagaca ggttacagaa tagtg                     45


<210> SEQ ID NO 9
<211> LENGTH: 45
<212> TYPE: DNA
<213> ORGANISM: Classical Swine Fever Virus

<400> SEQUENCE: 9

gagtcatgag tgcttgattg gtgccacaac tgtcaaggtg catgc                     45
```

-continued

```
<210> SEQ ID NO 10
<211> LENGTH: 45
<212> TYPE: DNA
<213> ORGANISM: Classical Swine Fever Virus

<400> SEQUENCE: 10

aaggaaaact tcctgtacat tcgcctacgc aaaaactctg aggaa                 45


<210> SEQ ID NO 11
<211> LENGTH: 45
<212> TYPE: DNA
<213> ORGANISM: Classical Swine Fever Virus

<400> SEQUENCE: 11

taccaacctg ttgcagccga agctataact caatggaacc tgagt                 45
```

*N*-LINKED GLYCOSYLATION ALTERATION IN E0 AND E2 GLYCOPROTEIN OF CLASSICAL SWINE FEVER VIRUS AND NOVEL CLASSICAL SWINE FEVER VIRUS VACCINE

This application is a divisional application of application Ser. No. 12/288,915, filed Oct. 24, 2008 now abandoned, which is herein incorporated by reference in its entirety.

BACKGROUND OF THE INVENTION

1. Field of the Invention

This invention relates to the characterization of the role that glycosylation of the transmembrane glycoprotein E2 of highly virulent Classical Swine Fever Virus (CSFV) strain Brescia plays during infection in the natural host and to the utilization of a strategy for manipulating the pattern of glycosylation for particular E2 glycosylation sites in order to alter CSFV virulence, providing a useful tool in the design and development of CSF live-attenuated vaccines.

2. Description of the Relevant Art

Classical swine fever (CSF) is a highly contagious disease of swine. The etiological agent, CSF virus (CSFV), is a small, enveloped virus with a positive, single-stranded RNA genome and, along with Bovine Viral Diarrhea Virus (BVDV) and Border Disease Virus (BDV), is classified as a member of the genus Pestivirus within the family Flaviridae (Becher et al. 2003. *Virology* 311: 96-104). The 12.5 kb CSFV genome contains a single open reading frame that encodes a 3898-amino-acid polyprotein and ultimately yields 11 to 12 final cleavage products ($NH_2$-Npro-C-$E^{rns}$-E1-E2-p7-NS2-NS3-NS4A-NS4B-NS5A-NS5B-COOH) through co- and post-translational processing of the polyprotein by cellular and viral proteases (Rice, C. M. 1996. In: *Fundamental Virology,* 3rd edition, Knipe et al., eds., Lippincott Raven, Philadelphia, Pa., pages 931-959).

Structural components of the CSFV virion include, the capsid (C) protein and the glycoproteins $E^{rns}$ (E0), E1, and E2. The glycoproteins E1 and E2 are anchored to the envelope at their carboxyl termini. $E^{rns}$ is also referred to as E0; E0 loosely associates with the viral envelope (Thiel et al. 1991. *J. Virol.* 65: 4705-4712; Weiland et al., 1990. *J. Virol.* 64: 3563-3569; Weiland et al. 1999. *J. Gen. Virol.* 80: 1157-1165). E1 and E2 are type I transmembrane proteins with an N-terminal ectodomain and a C-terminal hydrophobic anchor (Thiel et al, supra). E2 is considered essential for CSFV replication, as virus mutants containing partial or complete deletions of the E2 gene have proven non-viable (van Gennip et al. 2002. *Vaccine* 20: 1544-1556). E2 is the most immunogenic of the CSFV glycoproteins (Konig et al. 1995. *J. Virol.* 69: 6479-6486; van Gennip et al. 2000. *Vaccine* 19: 447-449; Weiland et al. 1990, supra), inducing neutralizing antibodies and protection against lethal CSFV challenge. E2 has been implicated, along with E0 (Hulst and Moormann. 1997. *J. Gen. Virol.* 78:2779-2787) and E1 (Wang et al. 2004. *Virology* 330:332-341), in viral adsorption to host cells; indeed, chimeric pestiviruses exhibit infectivity and cell tropism phenotypes consistent with those of the E2 gene donor (Liang et al. 2003. *J. Gen. Virol.* 84:1269-1274; van Gennip et al. 2000, supra). Modifications introduced into these glycoproteins appear to have an important effect on CSFV virulence (Meyers et al. 1999. *J. Virol.* 73: 10224-10235; Risatti et al., 2005a, *J. Virol.* 79: 3787-3796; Risatti et al. 2005b, *Virology* 343: 116-127; van Gennip et al. 2004. *J. Virol.* 78: 8812-8823).

Glycosylation is one of the most common types of protein modifications. N-linked oligosaccharides are added to specific asparagine residues in the context of the consensus sequence Asn-X-Ser/Thr (Kornfeld and Kornfeld. 1985. *Annu. Rev. Biochem.* 54: 631-664). Intracellular O-glycosylation is characterized by the addition of N-acetylglucosamine to serine and threonine residues in a protein, although the acceptor site does not display a definite consensus sequence (Gupta and Brunak. 2002. *Pac. Symp. Biocomput.* 310-322). Not all predicted sites in a protein sequence are used for carbohydrates, since many of them are inefficiently glycosylated (Shakin-Eshleman et al. 1992. *J. Biol. Chem.* 267: 10690-10698) or remain unglycosylated (Gavel and von Hejne. 1990. *Prot. Eng.* 3:433-442).

Putative N-glycosylation sites within CSFV E2 have been predicted previously (Moormann et al., 1990. *Vet Microbiol.* 23: 185-191; van Rijn et al. 1994. *J. Virol.* 68: 3934-3942). According to a glycosylation analysis algorithm (http://www.cbs.dtu.dk/services/), E2 of the CSFV strain Brescia has five putative N-linked and one putative O-linked glycosylation sites, although this is not confirmed by experimental evidence. A sixth N-linked glycosylation site is present in several CSFV strains, with the Brescia sequence differing in one amino acid from the consensus (Asn-X-Ser/Thr). Predicted E2 glycosylation sites are highly conserved among CSFV isolates. Even though glycosylation of E0, E1, or E2 proteins may play a significant role in the CSFV viral replication cycle, the function of added oligosaccharides is not known. In general, glycosylation of enveloped virus structural proteins has been shown to be important for receptor binding, membrane fusion, penetration, virus budding, and infectivity as analyzed in cultured cells (Abe et al. 2004. *J. Virol.* 78: 9605-9611; Doms et al. 1993. *Virology* 193: 545-562; Hanna et al. 2005. *J. Virol.* 79: 13262-13274; Shi et al. 2005. *J. Virol.* 79: 13725-13734; Shi and Elliott. 2004. *J. Virol.* 78: 5414-5422). However, the significance of viral envelope protein glycosylation in virus replication, pathogenesis, and virulence in the natural host is unknown. Recently, it has been shown that glycosylation of Porcine Respiratory and Reproductive Syndrome virus (PRRSV) GP5 affects virus infectivity, antigenicity and ability to induce neutralizing antibodies in swine (Ansari et al. 2006. *J. Virol.* 80: 3994-4004). Loss of N-linked glycosylation from the hemagglutinin-neuraminidase protein from Newcastle Disease Virus, a bird pathogen, results in attenuation of the virus in chickens (Panda et al. 2004. *J. Virol.* 78: 4965-4975). Similarly, degrees of virulence in chickens have been associated with glycosylation patterns of surface proteins hemagglutinin and neuraminidase of highly pathogenic avian influenza virus H5N1 (Hulse et al. 2004. *J. Virol.* 78: 9954-9964). Pathogenic phenotypes observed upon infection of natural hosts with modified viruses link glycosylation of virus surface proteins with mechanisms such as evasion of the immune system in PRRSV (Ansari et al., supra), attenuation in NDV (Panda et al., supra), and determinants of virulence in avian influenza (Hulse et al, supra).

Strategies for controlling disease in the event of a CSFV outbreak include the production of rationally designed live attenuated vaccine CSFV strains. Thus, the effect of modification of glycosylation sites of other of the CSFV virion glycoproteins need to be evaluated. Here, we report the effects of modification of particular E2 glycosylation sites. We used oligonucleotide site-directed mutagenesis of the E2 gene of the highly virulent CSFV strain Brescia to construct a panel of glycosylation mutants. These mutants were evaluated to determine whether the removal of each of these glycosylation sites in the E2 glycoprotein could affect viral infectivity and virulence in swine.

SUMMARY OF THE INVENTION

We have discovered glycosylation sites within the classical swine fever virus (CSFV) E2 glycoprotein where modification of the sites results in CSFV having novel virulence determinants.

In accordance with this discovery, it is an object of the invention to provide a recombinant CSFV comprising DNA encoding a modified CSFV E2 glycoprotein wherein specific glycosylation sites within E2 have been mutated resulting in an alteration in the site, i.e., the formerly glycosylated amino acid being altered and replaced by a non-glycosylated amino acid.

It is also an object of the invention to provide an isolated polynucleotide molecule comprising a genetically modified DNA sequence encoding a genetically modified infectious RNA molecule encoding a genetically modified CSFV. The CSFV is genetically modified such that when it infects a porcine animal it is unable to produce CSFV in the animal and it is able to elicit an effective immunoprotective response against infection by a CSFV in the animal. Mutated sequences or sequences homologous thereto contain a mutation that renders the encoded CSFV attenuated and able to elicit an effective immunoprotective response against infection by a CSFV in the animal.

It is additionally an object of the invention to provide an isolated infectious RNA molecule encoded by the isolated polynucleotide molecule recited above, and isolated infectious RNA molecules homologous thereto, which isolated infectious RNA molecules each encode a genetically modified CSFV, disabled in its ability to produce CSF.

An added object of the invention is to provide immunogenic compositions comprising a viable recombinant CSFV comprising a modified CSFV E2 glycoprotein displaying a glycosylation pattern different from that of the non-mutated E2 glycoprotein.

An additional object of the invention is to provide a rationally designed live attenuated CSFV vaccine which lessens severity of CSF disease when challenged with virulent Brescia CSFV wherein said vaccine comprises an altered glycosylation pattern as compared to that of the infectious, non-mutated virus.

Another object of the invention is to provide a rationally designed live attenuated CSFV vaccine effective to protect an animal from clinical CSF disease when challenged with virulent Brescia CSFV wherein said vaccine comprises an altered glycosylation pattern as compared to that of the infectious, non-mutated virus.

A further object of the invention is to provide a marker vaccine which allows a serological distinction between vaccinated animals and animals infected with CSFV.

A still further object of the invention is to provide a method for making a genetically modified CSFV, which method comprises mutating an infectious cDNA sequence, transforming the modified DNA into a modified infectious RNA molecule encoding a modified CSFV, and rescuing the genetically modified CSFV there from subsequent to said mutation.

Yet another object of the invention is to provide a method for protecting an animal against CSF by administering an effective amount of rationally designed live attenuated CSFV vaccine.

An additional object of the invention is to provide a method for delaying onset or severity of CSF in an animal by administering an effective amount of rationally designed live attenuated CSFV vaccine.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 4D: untreated BICv (lane 1), PNGase F-treated BICv (lane 2), untreated ΔO1N1-N6/N3v (lane 3).

FIG. 5A shows peripheral white blood cell and platelet counts in pigs infected with E2 glycosylation mutant viruses and parental BICv. Counts are expressed as numbers/ul of blood. Data represent means and standard deviations from at least two animals. FIG. 5B shows the virus titers in nasal, tonsil scrapings, and blood from pigs infected with E2 glycosylation mutants or BICv. Each point represents the mean log 10 $TCID_{50}$/ml and standard deviations from at least two animals. Sensitivity of virus detection: <log 10 1.8 $TCID_{50}$/ml.

DETAILED DESCRIPTION OF THE INVENTION

Virus glycoproteins are crucial in key steps of the virus cycle such as attachment to host cell receptors, entry, assembly of newly produced viral progeny, and exit. In vivo viral glycoproteins have been shown to influence infectivity (Ansari et al., supra), virulence (Hulse et al. and Panda et al., supra), and host immune response (Abe et al, supra). Added oligosaccharides confer proper function to viral glycoproteins since alteration of those glycosylation sites have shown dramatic consequences for viruses affecting protein folding (Herbert et al. 1997. *J. Cell Biol.* 139: 613-623; Land and Braakman. 2001. *Biochimie* 83: 783-790; Slater-Handshy et al., 2004. *Virology* 319: 36-48) and protein active conformation (Meunier et al. 1999. *J. Gen. Virol.* 80: 887-896). In this study, we analyzed glycosylation of the CSFV E2 glycoprotein in virus virulence in swine. All putative glycosylation sites in E2 were modified by site-directed mutagenesis using a full-length cDNA infectious clone of virulent strain Brescia as the target sequence (Risatti et al. 2005a, supra). Here, we showed that some of these sites have a major role in virulence and, protection; some of the sites seem to be critical for the production of viable virus. Interestingly, not all of the sites seem to be essential for in vitro or in vivo infectivity.

DNA encoding CSFV strain Brescia E2 glycoprotein contains 5 or 6 N-linked and one O-linked putative glycosylation sites (Retrieved from the Internet: <URL: www.cbs.dtu.dk/services/) (Moorman et al., supra). Sequence analysis of CSFV E2 glycoproteins showed that 5 of the N-linked glycosylation sites are highly conserved (N116, N121, N185, N229, N260); three of them, at CSFV E2 positions N116 (N1), N185 (N3), and N229 (N4) are also highly conserved among BVDV type I and II, and BDV (data not shown), implying an important role for these sites in all Pestiviruses. However, very little is known about the role of glycosylation on the function of Pestivirus glycoproteins. A previous study that examined closely related Pestivirus BVDV E2 glycoprotein expressed in a baculovirus/insect cell system (Pande et al. 2005. *Virus Res.* 114:54-62) showed that the pattern of glycosylation affects the ability of the isolated glycoprotein to prevent infection of calf testis cells with BVDV, an otherwise inhibitory effect observed with wild-type E2 protein (Hulst and Moormann, supra). The same study also showed that modification of N1 and N3 sites in BVDV E2 impaired expression and secretion of the protein in insect cells, suggesting that glycosylation at those sites is essential for correct folding and subsequent secretion of E2. Although these experiments were performed with a Baculovirus expression system and in our study we used recombinant viruses, the gathered evidence supports the idea that glycosylation at N1 and N3 sites are critical for E2 activity.

Figure 3:
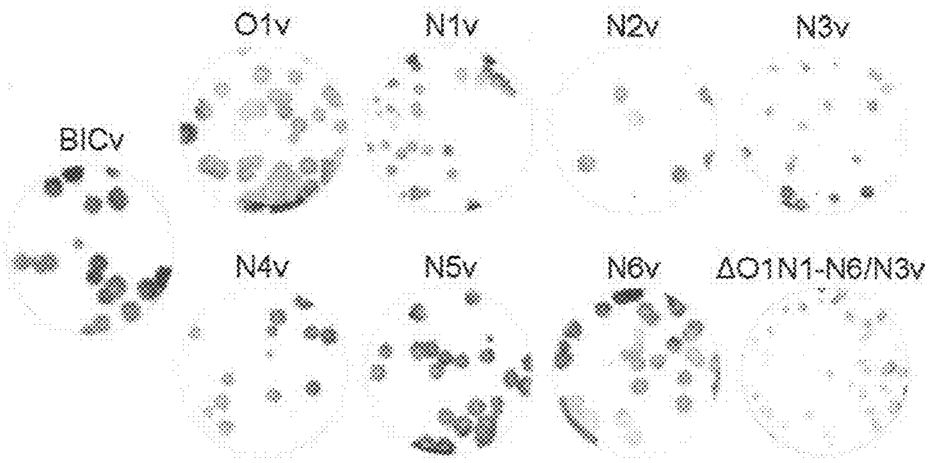
FIG. 3 shows plaque formation of E2 glycosylation mutants and BICv. SK6 monolayers were infected, overlaid with 0.5% agarose and incubated at 37° C. for 3 days. Plates were fixed with 50% (vol/vol) ethanol-acetone and stained by immunohistochemistry with mAb WH303 (Shi et al. 2005, supra).
Figure 4:
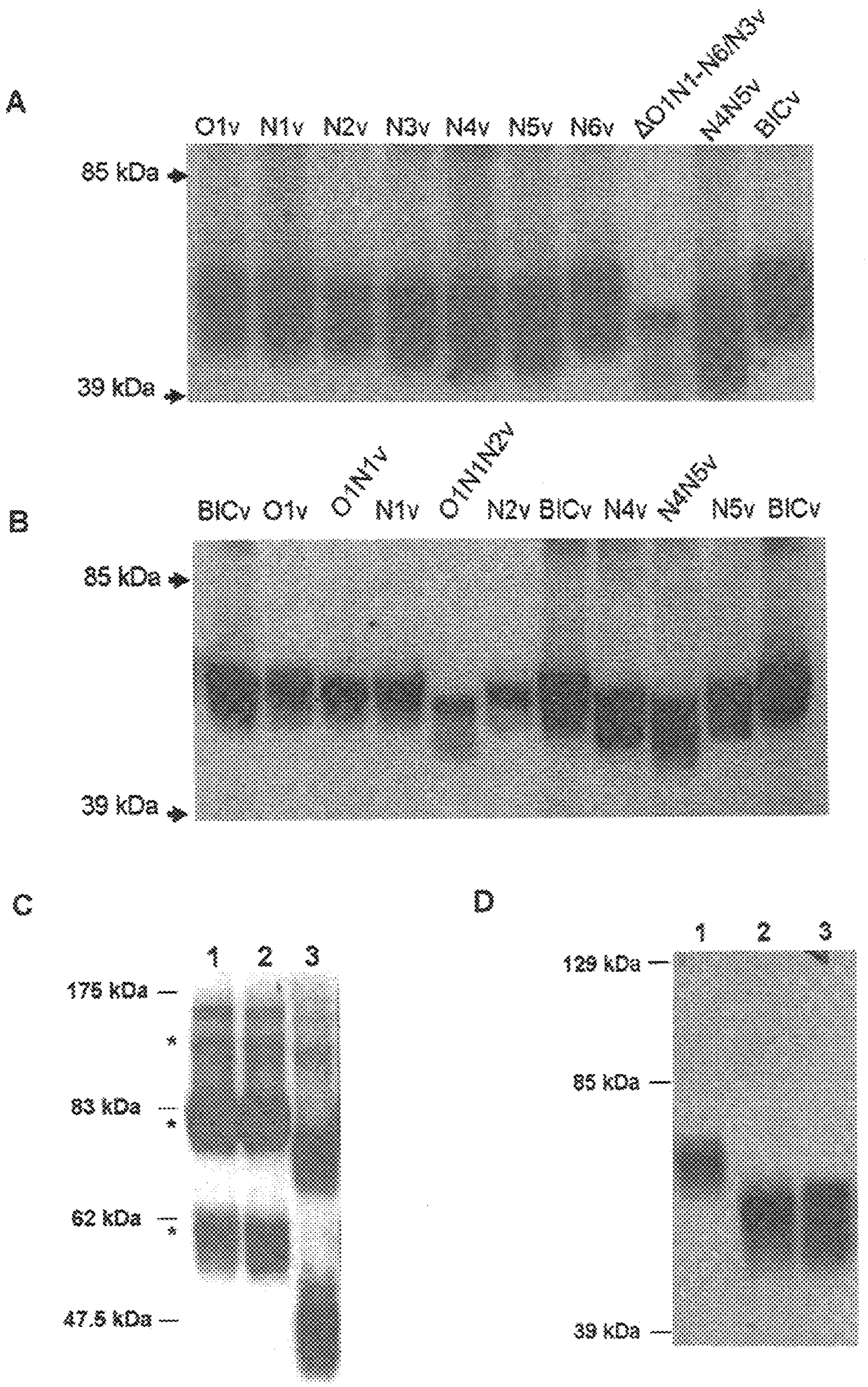
FIGS. 4A-4D depict analysis of E2 glycosylation mutants by Western immunoblots. SK6 monolayers were infected (MOI=1) with each of the mutants; parental BICv, or mock-infected and harvested 48 h post-infection. Cell lysates were run under reducing (FIGS. 4A, B and D) or non-reducing (FIG. 4C) conditions in 12% SDS-PAGE. CSFV E2 was detected with CSFV E2 monoclonal antibody WH303. For FIG. 4C: BICv (lane 1), N1v (lane 2), ΔO1N1-N6/N3v (lane 3). Asterisks indicate, from top to bottom, E2 homodimers, E1-E2 heterodimers and monomeric E2, respectively, as described by Weiland et al. (1990, supra).

Electrophoretic mobility analysis of the E2 glycoprotein in lysates obtained from infected SK-6 cells shows that amino acid residues N116 (N1v), N121 (N2v), N185 (N3v), N229 (N4v), and N260 (N5v) are used for carbohydrate addition (See FIG. 4, Example 5). In vitro growth characteristics and virus progeny yields of these mutants assessed in primary swine macrophage cultures, a CSFV natural target cell, were comparable to that of parental BICv, except for the mutant N3v (N185A) which demonstrated delayed growth kinetics (See FIG. 2A, Example 6). Suggestive of a role for CSFV E2 glycosylation patterns in virus attachment, entry, and/or exit from infected cells was the small plaque phenotype exhibited by single mutants N1v (N116A), N3v (N185A) and multiple mutant ΔO1N1-N6/N3v, in which a substantial plaque size reduction relative to parental BICv was observed in infected SK-6 cells (See FIG. 3, Example 6). Similarly, loss of one specific N-linked glycosylation site (G4) from the hemagglutinin-neuraminidase protein (HN) of Newcastle Disease Virus (NDV) yields plaques in cultured cells of considerably smaller size (Panda et al., supra), while three other single mutants (G1, G2, and G3) produced plaques comparable to the size of the parental virus. The G4 glycosylation site in NDV HN has been shown to be necessary for correct folding and transport of the protein to the cell surface of infected cells (McGinnes and Morrison. 1995. *Virology* 212: 398-410; Panda et al., supra). Interestingly, G4 virus was considerably attenuated in chickens (Panda et al., supra). In the case of CSFV, we have observed that other BICv-derived viruses containing recombinant E2 protein (Risatti et al. 2005a, supra) have shown reduced plaque size as well. Like N1v and ΔO1N1-N6/N3v here, those recombinant viruses were also attenuated in swine. In this study we also observed that mutant N3v showed a delayed growth kinetic in primary swine macrophage cell cultures. Further, mutant viruses showing plaque sizes smaller than parental BICv on SK-6 cells (FIG. 2A and FIG. 3) retained the capability of causing severe disease in swine (Table 3). These data suggest that changes in the E2 protein due to mutation N185A in N3v, unlike the N116A mutation in N1v, are not sufficient to alter virus range within the host.

Cleavage and glycosylation patterns of the hemagglutinin gene of H5 avian influenza viruses have been shown to affect pathogenicity in chickens (Deshpande et al. 1987. Proc. Natl. Acad. Sci. USA 84: 36-40; Horimoto and Kawaoka. 1994. *J. Virol.* 68: 3120-3128). More recently it has been shown that glycosylation patterns of the neuraminidase gene of highly pathogenic H5N1 avian flu viruses are important for increased virulence in chickens (Hulse, supra). The mechanisms by which these patterns affect avian flu virulence are unknown. Similarly, a single mutation (N1v) or multiple mutations (ΔO1N1-N6/N3v) within E2 rendered attenuated viruses with restricted in vivo replication ability (Tables 3 and 4). Unlike the acute fatal disease induced by BICv, infections caused by these mutants were sub-clinical in swine and characterized by decreased viral replication in target organs and reduced virus shedding. Interestingly, mutants O1v, N2v, N3v, N4v, N5v, and N6v retained the same capability of causing severe disease in swine as parental BICv, showing that in vivo E2 functions are retained and not influenced by the lack of glycans at positions N116, N121, N185, N229, and N260. As with avian flu, the genetic basis and the molecular mechanisms underlying CSFV virulence remain unknown.

As shown in this study, single mutations of E2 putative glycosylation sites have no effect on in vitro or in vivo infectivity of CSFV, with the exception of residue N116 in the N1v mutant. However, when multiple site mutations were introduced in E2, we observed that certain residue changes (O1N1N2N3, N1N2N3, N3N4N5, O1N1-N6) render nonviable viruses (data not shown). Conversely, when residue N185 (N3) was left unmodified in those clones, virus viability was not affected.

Production and manipulation of the isolated polynucleotide molecules described herein are within the skill in the art and can be carried out according to recombinant techniques described, among other places, in Sambrook et al. 1989. *Molecular Cloning: A Laboratory Manual,* 2d ed., Cold Spring Harbor Laboratory Press, Cold Spring Harbor, N.Y.

and Innis et al. (eds). 1995. *PCR Strategies*, Academic Press, Inc., San Diego, which are incorporated herein by reference.

The subject invention provides isolated polynucleotide molecules comprising genetically modified DNA sequences that encode genetically modified infectious RNA molecules that encode genetically modified Classical Swine Fever Viruses (CSFVs).

In particular, the subject invention provides an isolated polynucleotide molecule comprising a genetically modified DNA sequence encoding a genetically modified infectious RNA molecule that encodes a genetically modified CSFV, wherein said DNA sequences are SEQ ID NO:1 (N1v), SEQ ID NO:2 (ΔO1N1-N6/N3v), and SEQ ID NO:3 (N1 E0/2v) or sequences homologous thereto encoding the mutated viruses. Said DNA sequences encode infectious RNA molecules that are the RNA genomes of the mutated CSF viruses N1v and ΔO1N1-N6/N3v, respectively.

It is understood that terms herein referring to nucleic acid molecules such as "isolated polynucleotide molecule" and "nucleotide sequence include both DNA and RNA molecules and include both single-stranded and double-stranded molecules whether it is natural or synthetic origin.

For example, SEQ ID NO:1 is a DNA sequence corresponding to the genetically modified RNA genome of a genetically modified CSFV. Thus, a DNA sequence complementary to the DNA sequence set forth in SEQ ID NO:1 is a template for, i.e. is complementary to or "encodes", the RNA genome of the SF virus (i.e., RNA that encodes the CSFV).

Furthermore, when reference is made herein to sequences homologous to a sequence in the Sequence Listing, it is to be understood that sequences are homologous to a sequence corresponding to the sequence in the Sequence Listing and to a sequence complementary to the sequence in the Sequence Listing.

An "infectious RNA molecule", for purposes of the present invention, is an RNA molecule that encodes the necessary elements for viral replication, transcription, and translation into a functional virion in a suitable host cell, provided, if necessary, with a peptide or peptides that compensate for any genetic modifications, e.g. sequence deletions, in the RNA molecule.

An "isolated infectious RNA molecule" refers to a composition of matter comprising the aforementioned infectious RNA molecule purified to any detectable degree from its naturally occurring state, if such RNA molecule does indeed occur in nature. Likewise, an "isolated polynucleotide molecule" refers to a composition of matter comprising a polynucleotide molecule of the present invention purified to any detectable degree from its naturally occurring state, if any.

For purposes of the present invention, two DNA sequences are substantially homologous when at least 80% (preferably at least 85% and most preferably 90%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a modified CSFV E2 glycopeptide (N1v, ΔO1N1-N6/N3v, or N1E0/2v) and which hybridize under stringent conditions, as described herein, to the modified CSFV E2 sequences disclosed herein, i.e., SEQ ID NO:1 (N1v) or SEQ ID NO:2 (ΔO1N1-N6/N3v) or SEQ ID NO:3 (N1E0/2v) or to fragments thereof, are encompassed by the present invention. Fragments of a nucleotide sequence that are useful as hybridization probes may not encode fragment proteins retaining biological activity.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context, of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and, identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The skilled artisan, having the benefit of the sequences as reported herein, may now use all or a substantial, portion of the disclosed sequences for purposes known to those skilled in this art. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of one of the CSFV E2 glycoproteins of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, a modified CSFV E2 glycoprotein activity, i.e., N1v, ΔO1N1-N6/N3v, or N1E0/2v glycoprotein activity as described herein. Such variants may result from, for example, genetic polymorphism or from human manipulation. Biologically active variants of a modified CSFV E2 glycoprotein of the invention, i.e., N1v or ΔO1N1-N6/N3v or N1E0/2v, will have at least about 90%, preferably at least about 95%, and more preferably at least about 98% sequence identity to the amino acid sequence for the native, protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired modified CSFV E2 glycoprotein activity, i.e., N1v or ΔO1N1-N6/N3v or N1E0/2v glycoprotein activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of modified CSFV E2 glycoprotein, i.e., N1v, ΔO1N1-N6/N3v, or N1E0/2v glycoprotein activity, can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "CSF" encompasses disease symptoms in swine caused by a CSFV infection. Examples of such symptoms include, but are not limited to, anorexia, depression, fever, purple skin discoloration, staggering gait, diarrhea and cough. As used herein, a CSFV that is "unable to produce CSF" refers to a virus that can infect a pig, but which does not produce any disease symptoms normally associated with a CSF infection in the pig, or produces such symptoms, but to a lesser degree, or produces a fewer number of such symptoms, or both.

The terms "porcine" and "swine" are used interchangeably herein and refer to any animal that is a member of the family Suidae such as, for example, a pig. "Mammals" include any warm-blooded vertebrates of the Mammalia class, including humans.

The terms "classical swine fever virus" and "CSFV", as used herein, unless otherwise indicated, mean any strain of CSF viruses.

The term "open reading frame", or "ORF", as used herein, means the minimal nucleotide sequence required to, encode a particular CSFV protein without an intervening stop codon.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly porcine cells, and are described in further detail below.

A "functional virion" is a virus particle that is able to enter a cell capable of hosting a CSFV, and express genes of its particular RNA genome (either an unmodified genome or a genetically modified genome as described herein) within the cell. Cells capable of hosting a CSFV include swine kidney cells (SK6) and primary porcine macrophage cell cultures. Other mammalian cells, especially other porcine cells, may also serve as suitable host cells for CSF virions.

The isolated polynucleotide molecules of the present invention encode CSF viruses that can be used to prepare live attenuated vaccines using art-recognized methods for protecting swine from infection by a CSFV, as described in further detail below. Furthermore, these isolated polynucleotide molecules are useful because they can be mutated using molecular biology techniques to encode genetically-modified CSF viruses useful, inter alia, as vaccines for protecting swine from CSF infection. Such genetically-modified CSF viruses, as well as vaccines comprising them, are described in further detail below.

Accordingly, the subject invention further provides a method for making a genetically modified CSFV, which method comprises mutating the DNA sequence encoding an infectious RNA molecule which encodes the CSFV as described above, and expressing the genetically modified CSFV using a suitable expression system. A CSFV, either wild-type or genetically modified, can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro.

The term "genetically modified", as used herein and unless otherwise indicated, means genetically mutated, i.e. having one or more nucleotides replaced, deleted and/or added. Polynucleotide molecules can be genetically mutated using recombinant techniques known to those of ordinary skill in the art, including by site-directed mutagenesis, or by random mutagenesis such as by exposure to chemical mutagens or to radiation, as known in the art.

The subject invention further provides an isolated polynucleotide molecule comprising a DNA sequence encoding an infectious RNA molecule which encodes a genetically modified CSFV that is unable to produce CSF in a porcine animal, wherein the DNA sequence encoding the infectious RNA molecule encoding said modified CSFV is SEQ ID NO:1, SEQ ID NO:2, SEQ ID NO:3 or sequences homologous thereto, contains one or more mutations that genetically disable the encoded CSFV in its ability to produce CSF. "Genetically disabled" means that the CSFV is, unable to produce CSF in a swine animal infected therewith.

In one embodiment, the genetically modified CSFV disabled in its ability to cause CSF is able to elicit an effective immunoprotective response against infection by a CSFV in a swine animal. Accordingly, the subject invention also provides an isolated polynucleotide molecule comprising a DNA sequence encoding an infectious RNA molecule which encodes a CSFV that is genetically modified such that when it infects a porcine animal it a) is unable to produce CSF in the animal, and b) is able to elicit an effective immunoprotective response against infection by a CSFV in the animal, wherein the DNA sequence encoding said modified CSFV is SEQ ID NO:1 (N1v), SEQ ID NO:2 (ΔO1N1-N6/N3v), or SEQ ID NO:3 (N1E0/2v) or sequences homologous thereto, contains one or more mutations that genetically disable the encoded CSFV in its ability to produce CSF.

The term "immune response" for purposes of this' invention means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

An "antigenic epitope" is, unless otherwise indicated, a molecule that is able to, elicit an immune response in a particular animal or species. Antigenic epitopes are proteinaceous molecules, polypeptide sequences, optionally comprising non-protein groups such as carbohydrate moieties and/or lipid moieties.

The genetically modified CSF viruses encoded by the above-described isolated polynucleotide molecules are, in one embodiment, able to elicit an effective immunoprotective response against infection by a CSFV. Such genetically modified CSF viruses are preferably able to elicit an effective immunoprotective response against any strain of CSF viruses.

In one embodiment, the mutation or mutations in the isolated polynucleotide molecule encoding the genetically disabled CSFV are non-silent and occur in one or more open reading frames of the nucleotide sequence encoding the CSFV.

As used herein, unless otherwise indicated, "coding regions" refer to those sequences of RNA from which CSFV proteins are expressed, and also refer to cDNA that encodes such RNA sequences. Likewise, "ORFs" refer both to RNA sequences that encode CSFV proteins and to cDNA sequence encoding such RNA sequences.

Determining suitable locations for a mutation or mutations that will encode a CSFV that is genetically disabled so that it is unable to produce CSF yet remains able to elicit an effective immunoprotective response against infection by a CSFV can be made based on SEQ ID NO:1, SEQ ID NO:2 and SEQ ID NO:3 provided herein. One of ordinary skill can refer to the sequence of the infectious cDNA clone of CSFV provided by this invention, make sequence changes which will result in a mutation altering the glycosylation pattern of the glycoprotein, and test the viruses encoded thereby both for their ability to produce CSF in swine, and to elicit an effective immunoprotective response against infection by a CSFV. In so doing, one of ordinary skill can refer to techniques known in the art and also those described and/or exemplified herein.

For example, an ORF of the sequence encoding the infectious RNA molecule encoding the CSFV can be mutated and the resulting genetically modified CSFV tested for its ability to cause CSF.

In a further preferred embodiment, an antigenic epitope of the genetically modified CSFV of the present invention is a detectable antigenic epitope. Such isolated polynucleotide molecules and the CSF viruses they encode are useful, inter alia, for studying CSF infections in swine, determining successfully vaccinated swine, and/or for distinguishing vaccinated swine from swine infected by a wild-type CSFV. Preferably, such isolated polynucleotide molecules further contain one or more mutations that genetically disable the encoded CSFV in its ability to produce CSF, and more preferably are able to elicit an effective immunoprotective response in a porcine animal against infection by a CSFV.

Antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present invention can be found in texts recognized in the art, such as Coligan, J. E., et al. (eds), 1998, *Current Protocols in Immunology*, John Willey & Sons, Inc., which is hereby incorporated by reference in its entirety. Alternatively, the antigenic epitope itself can be detected by, for example, contacting samples that potentially comprise the antigenic epitope with fluorescently-labeled antibodies or radioactively-labeled antibodies that specifically bind to the antigenic epitopes.

The present invention further provides an isolated polynucleotide molecule comprising a DNA sequence encoding an infectious RNA molecule which encodes a genetically modified CSFV that detectably lacks a CSFV antigenic epitope, wherein the DNA sequence encoding the RNA molecule encoding, the modified CSFV is SEQ ID NO:1 (N1v) or SEQ ID NO:2 (ΔO1N1-N6/N3v) or SEQ ID NO 3 (N1E0/2v) or sequences homologous thereto, except that it lacks one or more nucleotide sequences encoding a detectable CSFV antigenic epitope. Such isolated polynucleotide molecules are useful for distinguishing between swine infected with a recombinant CSFV of the present invention and swine infected with a wild-type CSFV. For example, animals vaccinated with killed, live or attenuated CSFV encoded by such an isolated polynucleotide molecule can be distinguished from animals infected with wild-type CSF based on the absence of antibodies specific to the missing antigenic epitope, or based on the absence of the antigenic epitope itself: If antibodies specific to the missing antigenic epitope, or if the antigenic epitope itself, are detected in the animal, then the animal was exposed to and infected by a wild-type CSFV. Means for detecting antigenic epitopes and antibodies specific thereto are known in the art, as discussed above. Preferably, such an isolated polynucleotide molecule further contains one or more mutations that genetically disable the encoded CSFV in its ability to produce CSF. More preferably, the encoded virus remains able to elicit an effective immunoprotective response against infection by a CSFV.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., *Remington's Pharmaceutical Science,* 18th ed., 1990, Mack Publishing, which is incorporated herein by reference.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN™ adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN™ 85 detergent (ICI Surfactants), 0.7% (v/v) TWEEN™ 80 detergent (ICI Surfactants), 2.5% (v/v) ethanol, 200 μg/ml Quil A, 100 μg/ml cholesterol, and 0.5% (v/v) lecithin. Modified SEAM 1/2 is an oil-in-water emulsion comprising 5% (v/v) squalene, 1% (v/v) SPAN™ 85 detergent, 0.7% (v/v) Tween 80 detergent, 2.5% (v/v) ethanol, 100 μg/ml Quil A, and 50 μg/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including Domb et al. 1992. *Polymers for Advanced Technologies* 3: 279-292, which is incorporated herein by reference. Additional guidance in selecting, and using polymers in pharmaceutical formulations can be found in texts known in the art, for example M. Chasin and R. Langer (eds), 1990, "Biodegradable Polymers as Drug Delivery Systems" in *Drugs and the Pharmaceutical Sciences, Vol.* 45, M. Dekker, NY, which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 g to about 100 mg, more preferably from about 1 μg to about 10 mg, even more preferably from about 10 μg to about 1 mg. The dose amount of an infectious RNA molecule of the present invention in a vaccine of the present invention preferably ranges from about 0.1 μg to about 100 mg, more preferably from about 1 μg to about 10 mg, even more preferably from about 10 μg to about 1 mg. The dose amount of a viral vector of the present invention in a vaccine of the present invention preferably ranges from, about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

In summary, our studies determined the utilization of five potential N-glycosylation sites in the CSFV strain Brescia E2 protein. Individual N-linked glycosylation sites are not essential for viral particle formation or virus infectivity in cultured swine macrophages or the natural host, with one individual site, N116, involved in attenuation of the virulent parental virus. This study also showed that in the context of three or more putative glycosylation site modifications, residue N185 is critical for virus viability. The effective protective immunity elicited by N1v suggests that glycosylation of E2 could be modified for the development of live-attenuated vaccines. An improved understanding of the genetic basis of virus virulence and host range will permit future rational design of efficacious biological tools for controlling CSF.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

Swine kidney cells (SK6) (Terpstra et al., supra) free of Bovine Viral Diarrhea Virus (BVDV) were cultured in Dulbecco's Minimal Essential Medium (DMEM, GIBCO, Grand Island, N.Y.) with 10% fetal calf serum (FCS, Atlas Biologicals, Fort Collins, Colo.). CSFV Brescia strain (obtained from the Animal and Plant Health Inspection Service, Plum Island Animal Disease Center) was propagated in SK6 cells and used for the construction of an infectious cDNA clone (Risatti et al. 2005a, supra). Growth kinetics were assessed on primary swine macrophage cell cultures prepared as described by Zsak et al. (1996. *J. Virol.* 70: 8865-8871). Titration of CSFV from clinical samples was performed using SK6 cells in 96-well plates (Costar, Cambridge, Mass.). Viral infectivity was detected, after 4 days in culture, by an immunoperoxidase assay using the CSFV monoclonal antibodies (mAbs) WH303 (Edwards et al. 1991. *Vet. Microbial.* 29:101-108) and the Vectastain ABC kit (Vector Laboratories, Burlingame, Calif.). Titers were calculated using the method of Reed and Muench (1938. *American J. Hygiene* 27:493-497) 497) and expressed as $TCID_{50}$/ml. As performed, test sensitivity was ≥log 10 1.8 $TCID_{50}$/ml. Plaque assays were performed using SK6 cells in 6-well plates (Costar). SK6 monolayers were infected, overlaid with 0.5% agarose and incubated at 37° C. for 3 days. Plates were fixed with 50% (vol/vol) ethanol-acetone and, stained by immunohistochemistry with mAb WH303 (Risatti et al. 2003. *J. Clin. Microbial.* 41: 500-505).

Example 2

Construction of CSFV Glycosylation Mutants

A full-length infectious clone of the virulent Brescia isolate (pBIC) (Risatti et al. 2005a, supra) was used as a template in which putative O- and N-linked glycosylation sites in the E2 glycoprotein were mutated. Glycosylation sites were predicted using analysis tools from the Center for Biological Sequence Analysis (Retrieved from the Internet: <URL: www.cbs.dtu.dk/services/). Mutations were introduced by site-directed mutagenesis using the QuickChange XL Site-Directed Mutagenesis kit (Stratagene, Cedar Creek, Tex.) performed per manufacturer's instructions and using the following primers (only forward primer sequences are shown); O1v: CATCATTACATAAGG ACGCTTTAGCCACTTC-CGTGACATTCGAGC (SEQ ID NO:4); N1v: CCCTG-TAGT CAAGGGAAAGTACGCCACAACCTTGT-TGAATGGTAG (SEQ ID NO:5); N2v: AAA GTACAACACAACCTTGTTGGCTGGTAGT-GCATTCTACCTAGT(SEQ ID NO:6); N3v: ATTCTACTG-TAAATGGGGGGGCGCTTGGACATGTGT-GAAAGGTGA (SEQ ID NO:7); N4v: ATAGGTAAGTGCATTTTGGCAGCTGAGA-CAGGTTACAGAATAGTG (SEQ ID NO:8); N5v: GAGT-CATGAGTGCTTGATTGGTGCCACAACT-GTCAAGGTGCATGC (SEQ ID NO:9); N6v: AAGGAAAACTTCCTGTACATTCGC-CTACGCAAAAACTCTGAG GAA (SEQ ID NO:10). N1E0/2v cDNA infectious clone was constructed using N1E2 as template deleting the putative glycosylation site at N269 using the forward primer: TACCAACCTGTTGCAGC-CGAAGCTATAACTCAATGGAACCTGAGT (SEQ ID NO:11; Fernandez Sainz et al. 2008. *Virology* 370: 122-129).

Example 3

In Vitro Rescue of CSFV Brescia and Glycosylation Mutants

Full-length genomic clones were linearized with Srfl and in vitro transcribed using the 17 Megascript system (Ambion, Austin, Tex.). RNA was precipitated with LiCl and transfected into SK6 cells by electroporation at 500 volts, 720 ohms, 100 watts with a BTX 630 electroporator (BTX, San Diego, Calif.). Cells were seeded in 12-well plates and incubated for 4 days at 37EC and 5% $CO_2$. Virus was detected by immuno-peroxidase staining as described above, and stocks of rescued viruses were stored at −70EC.

Figure 1:
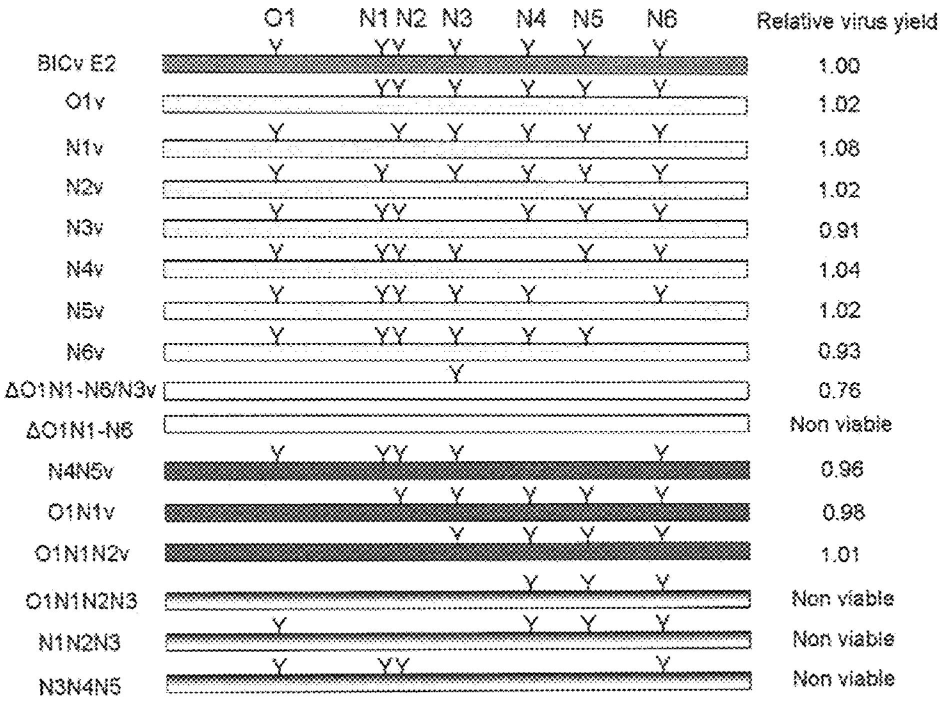
FIG. 1 is a schematic representation of glycosylation mutants of Classical Swine Fever Virus E2 protein, generated by site-directed mutagenesis of a cDNA full-length clone pBIC (Shakin-Eshleman et al., supra). The BICv wild type E2 glycoprotein is shown at the top. Y: putative glycosylation sites. Mutants were named with an O (O-linked glycosylation) or an N(N-linked glycosylation) followed by a number that represents the relative position of putative glycosylation sites within E2 amino acid sequence (76, 116, 121, 185, 229, 260, 297). Relative virus yield is the final point virus yield as a proportion of the final end point (72 hours post-infection) virus yield of parental BICv.

Infectious RNA was in vitro transcribed from full-length infectious clones of the CSFV Brescia strain or a set of glycosylation mutants (Table 1, FIG. 1) and used to transfect SK6 cells. Mutants referred to as O1, N1, N2, N3, N4, N5, and N6 represent each of seven putative glycosylation sites starting from the N terminus of E2 (Table 1), whereas multiple mutants are represented by combinations of indicated sites (FIG. 1). Viruses were rescued from transfected cells by day 4 post-transfection. Nucleotide sequences of the rescued virus genomes were identical to parental DNA plasmids, confirming that only mutations at predicted glycosylation sites were reflected in rescued viruses.

TABLE 1

Set of CSFV E2 glycosylation mutant viruses constructed.

| E2Position | Wild-Type Sequence | Mutant Sequence | Codon Change | Mutant |
|---|---|---|---|---|
| 75 | P | A | CCC→GCC | O1v |
| 116 | NTTL | ATTL | AAC→GCC | N1v |
| 121 | NGSA | AGSA | AAT→GCT | N2v |
| 185 | NWTC | AWTC | AAC→GCC | N3v |
| 229 | NETG | AETG | AAT→GCT | N4v |
| 260 | NTTV | ATTV | AAC→GCC | N5v |
| 297 | NYAK | AYAK | AAC→GCC | N6v |

TABLE 1-continued

Set of CSFV E2 glycosylation mutant viruses constructed.

| E2Position | Wild-Type Sequence | Mutant Sequence | Codon Change | Mutant |
|---|---|---|---|---|
| 75, 116, 121, 229, 260, 297 | P, NTTL, NGSA, NETG, NTTV, NYAK | A, ATTL, AGSA, AETG, ATTV, AYAK | CCC→GCC, AAC→GCC, AAT→GCT, AAT→GCT, AAC→GCC, AAC→GCC | ΔO1N1-N6/N3v |
| 75, 116 | P, NTTL | A/ATTL | CCC→GCC, AAC→GCC | O1N1v |
| 75, 116, 121 | P, NTTL, NGSA | A, ATTL, AGSA | CCC→GCC, AAC→GCC, AAT→GCT | O1N1N2v |
| 229, 260 | NETG, NTTV | AETG, ATTV | AAT→GCT, AAC→GCC | N4N5v |

Example 4

DNA Sequencing and Analysis

Full-length infectious clones and in vitro rescued viruses were completely sequenced with CSFV specific primers by the dideoxynucleotide chain-termination method (Sanger et al. 1977. *Proc. Natl. Acad. Sci. USA* 74: 5463-5467). Viruses recovered from infected animals were sequenced in the mutated area. Sequencing reactions were prepared with the Dye Terminator Cycle Sequencing Kit (Applied Biosystems, Foster City, Calif.). Reaction products were sequenced on a PRISM 3730xl automated DNA Sequencer (Applied Biosystems). Sequence data were assembled with the Phrap software program (http://www.phrap.org), with confirmatory assemblies performed using CAP3 (Huang et al. 1999. *Genome Res.* 9: 868-877). The final DNA consensus sequence represented an average five-fold redundancy at each base position. Sequence comparisons were conducted using BioEdit software (Retrieved from the Internet: <URL: www-.mbio.ncsu.edu/BioEdit/bioedit.html).

Example 5

Western Blot Analysis

Glycosylation status of the E2 glycoprotein of BICv and mutant viruses was analyzed in lysates of SK6 infected cells by Western immunoblots. CSFV E2 was detected with mAb WH303. SK6 monolayers were infected (multiplicity of infection, MOI=1) with BICv or glycosylation mutants harvested at 48 h post-inoculation (HPI) using the NuPAGE LDS sample buffer system (Invitrogen, Carlsbad, Calif.), and incubated at 80° C. for 20 min. Samples were run under reducing or non-reducing conditions in pre-cast NuPAGE 12% Bis-Tris acrylamide gels (Invitrogen). Western immunoblots were performed using the WesternBreeze Chemoluminescent Immunodetection System (Invitrogen).

Treatment of infected cell extracts with Peptide: N-glycosidase F (PNGase F) (New England BioLabs, Ipswich, Mass.) was performed following manufacturer's directions. Briefly, infected cell extracts were denatured at 100° C. for 10 min in Glycoprotein Denaturing Buffer (New England BioLabs). The reaction was then put on ice for 5 minutes and PNGase F digestion was performed for 20 hr in the presence of 1% NP-40.

Relative electrophoretic mobility of E2 was analyzed by Western blot in lysates of SK-6 cells infected with different mutant and parental BICv viruses using mAb WH303. Assuming that differences in E2 mobility among mutants and parental viruses are likely due to the number of carbohydrate moieties attached to the protein, we observed that E2 from single mutants N1v, N2v, N3v, N4v, and N5v migrated further than E2 from mutants O1v, N6v, or parental BICv (FIGS. 4A and B). The data suggested that, while N1, N2, N3, N4, N5 sites are targeted for the addition of glycans in swine cells, O1 and N6 sites (Table 1) are not used for glycosylation of BICv E2. Those observations were further confirmed by analyzing the mobility of E2 in lysates from cells infected with mutant viruses missing two or more putative glycosylation sites (FIG. 1; FIGS. 4A and 4B). For example, double mutant O1N1v E2 migrated faster than O1v and BICv E2, but paralleled N1v E2 mobility (FIG. 4B). Triple mutant O1N1N2v E2 protein migrated faster than N1v or N2v E2 proteins (FIG. 4B), probably due to the additive effect of the mobility shift caused by lack of glycans at both N1 and N2 sites. N3v E2, like N2v E2, migrated quicker than parental BICv E2 (FIG. 4A). As observed with O1N1N2v, double mutant N4N5v E2 migrated further than N4v and N5v E2 proteins (FIG. 4B), suggesting that the disparity in mobility is due to the absence of both glycosylation sites. The largest change in E2 mobility was observed with multiple site mutant ΔO1N1-N6/N3v. This virus is deficient in four of five N-linked glycosylation sites that showed different E2 migration patterns (FIG. 4A). Overall, our data firmly suggests that CSFV E2 N1, N2, N3, N4 and N5 sites (FIG. 1) are targeted for glycosylation in swine SK-6 cells.

Absence of glycosylation in N1 and ΔO1N1-N6/N3 viruses does not affect the formation of E2 homo- and heterodimers (FIG. 4C). Western blot analysis performed with extracts of SK6 cells infected with either of the viruses and run under non-reducing conditions demonstrated the presence of bands with apparent molecular masses of 50, 66 and 90 to 100 kDa corresponding to E2 monomers, E2-E1 heterodimers, and E2 homodimers, respectively, as previously described by Weiland et al. (1990, supra). The pattern of bands was maintained in N1 and ΔO1N1-N6/N3 viruses with the expected shift in their electrophoretic mobility. Therefore, mutations of CSFV N-linked glycosylation sites would not affect E2 dimerization in infected cells.

Treatment of SK6 BICv-infected cell extracts with Peptide N-glycosidase F (PNGase F) effectively removed N-linked glycosylation, resulting in a protein that migrated with a slightly faster electrophoretic mobility than the E2 ΔO1N1-N6/N3v protein (FIG. 4D). This is expected, since digestion with PNGase F would generate completely unglycosylated proteins, whereas ΔO1N1-N6/N3v E2 protein still conserves the N3-linked glycosylation site.

Example 6

In Vitro and In Vivo Analysis of Glycosylation Mutants

Figure 2:
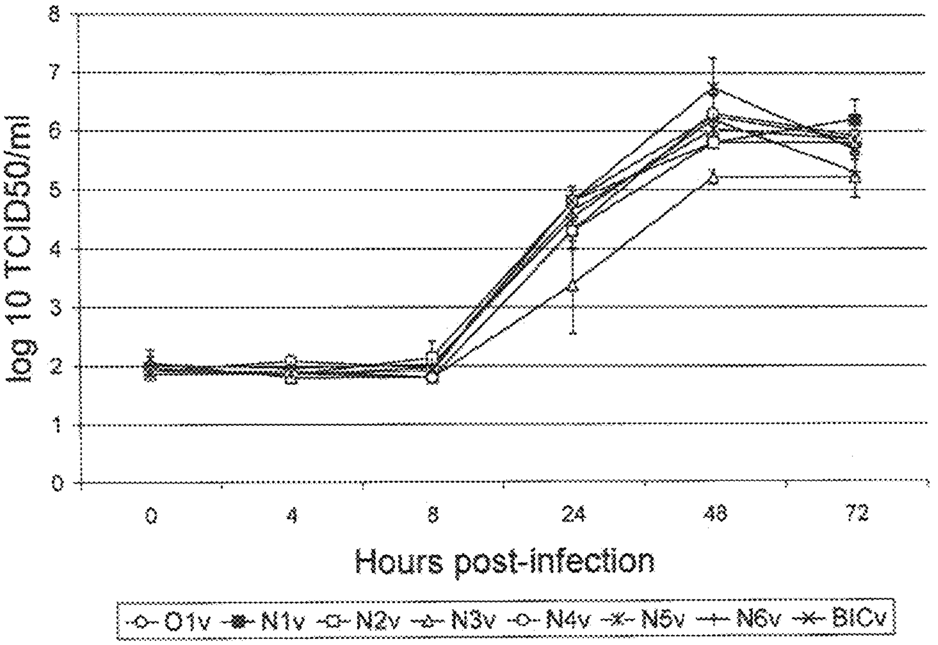
FIGS. 2A and 2B depict the in vitro growth characteristics of E2 individual (A) and multiple (B) glycosylation mutants and parental BICv. Primary swine macrophage cell cultures were infected (MOI=0.01) with each of the mutants or BICv and virus yield was titrated at times post infection in SK6 cells. Data represent means and standard deviations from two independent experiments. Sensitivity of virus detection: <log 10 1.8 $TCID_{50}$/ml.
Figure 2:
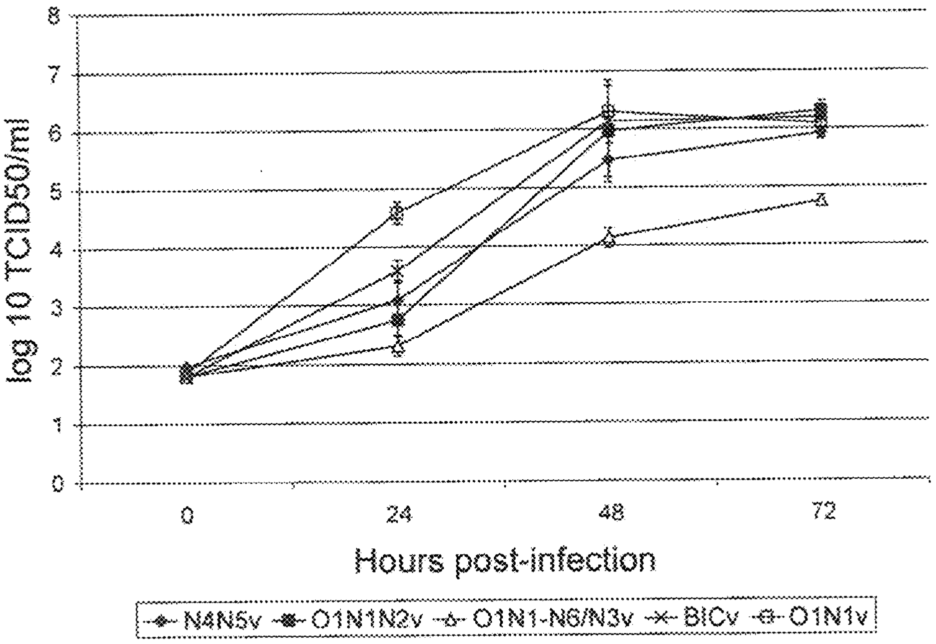

In vitro growth characteristics of mutant viruses O1v, N1v, N2v, N3v, N4v, N5v, N6v and multiple site mutants ΔO1N1-N6/N3v, O1N1v, O1N1N2v, and N4N5v were evaluated relative to parental BICv in a multistep growth curve (FIGS. 2A and 2B). Primary swine macrophage cell cultures were infected at a multiplicity of infection (MOI) of 0.1 $TCID_{50}$ per cell. Virus was adsorbed for 1 h (time zero), and samples were collected at times post-infection through 72 h.

All single glycosylation site mutants, except N3v, exhibited growth characteristics practically indistinguishable from BICv. N3v exhibited a lower rate of growth and a 10-fold decrease in the final virus yield (FIG. 2A). Multiple glycosylation site mutant ΔO1N1-N6/N3v also exhibited delayed growth and reduced viral yield when compared with multiple site mutants N4N5v, O1N1v, and O1N1N2v and parental BICv (FIG. 2B). Additionally, when viruses were tested for their plaque size in SK6 cells, N1v, N3v, and ΔO1N1-N6/N3v exhibited a noticeable reduction in plaque size relative to BICv (FIG. 3). Interestingly, viruses were not rescued from SK-6 cells transfected with RNA transcribed from full-length cDNA clones carrying multiple glycosylation site mutations (ΔO1N1-N6, O1N1N2N3, N1N2N3, and N3N4N5) that included substitutions at the N3 position (N185).

Each of the glycosylation mutants was initially screened for its virulence phenotype in swine relative to virulent Brescia virus. Swine used in all animal studies were 10 to 12 weeks old, forty-pound commercial bred pigs inoculated intranasally with $10^5$ $TCID_{50}$ of either mutant or wild-type virus. For screening, 18 pigs were randomly allocated into 9 groups of 2 animals each, and pigs in each group were inoculated with one of the single glycosylation mutants, ΔO1N1-N6/N3v or BICv. Clinical signs (anorexia, depression, fever, purple skin discoloration, staggering gait, diarrhea and cough) and changes in body temperature were recorded daily throughout the experiment and scored as previously described (Mittelholzer et al. 2000. Vet. Microbiol. 74: 293-308), with modifications.

To assess the effect of the N1v mutation on virus shedding and distribution in different organs during infection, pigs were randomly allocated into 2 groups of 9 animals each and intranasally inoculated (see above) with N1v or BICv. One pig per group was sacrificed at 2, 4, 6, 8 and 12 DPI. Blood, nasal swabs and tonsil scraping samples were obtained from pigs at necropsy. Tissue samples (tonsil, mandibular lymph node, spleen and kidney) were snap-frozen in liquid nitrogen for subsequent virus titration. The remaining 4 pigs in each room were monitored to check for appearance of clinical signs during a 21-day period.

Figure 5:
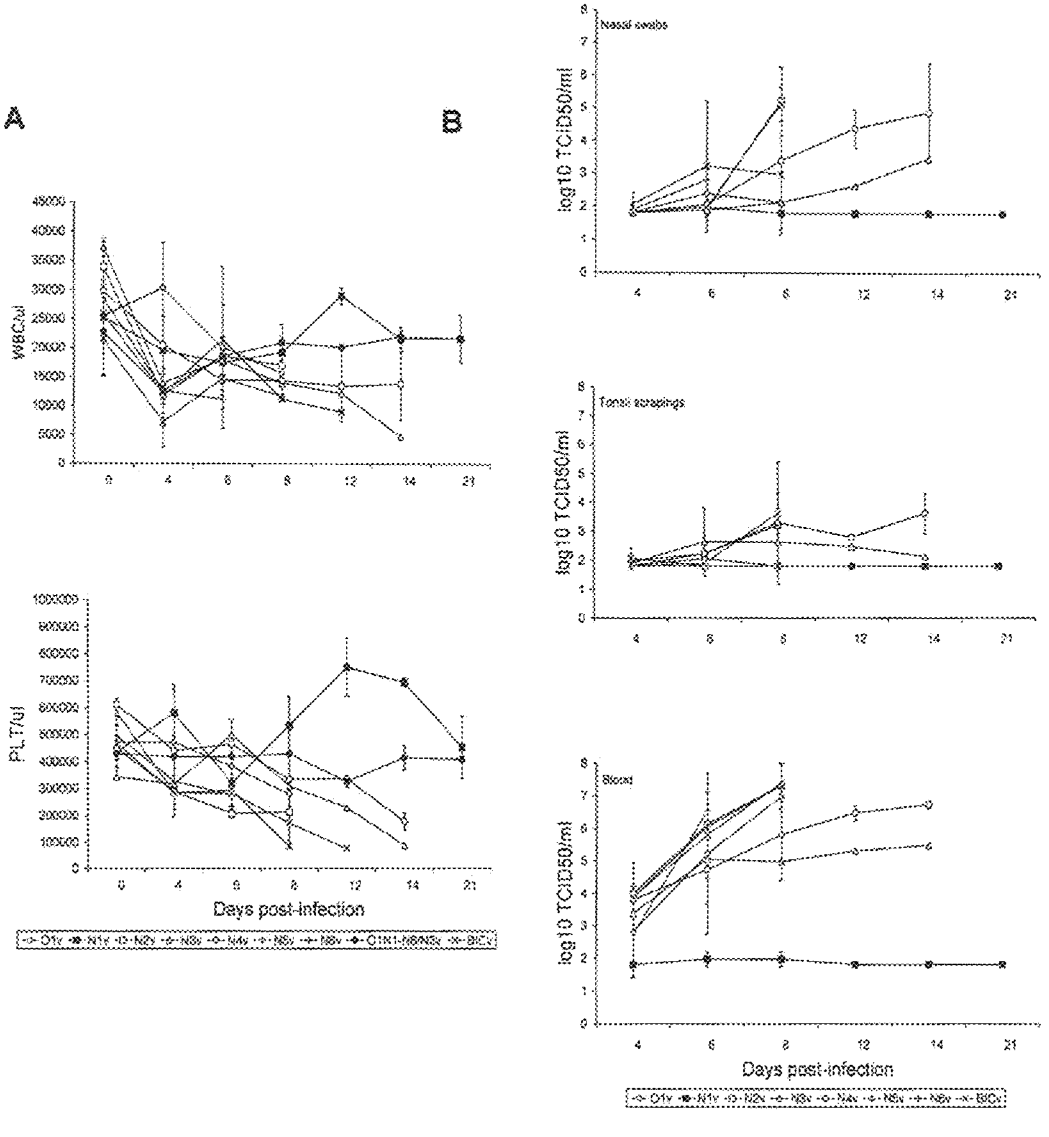
FIGS. 5A and 5B depict hematological data and virus titers in clinical samples from animals infected with CSFV E2 glycosylation mutants and parental BICv.

To examine the effect of E2 glycosylation on CSFV virulence, pigs were intranasally inoculated with $10^5$ $TCID_{50}$ of the ΔO1N1-N6/N3v mutant (Table 1) and monitored for clinical disease. This mutant, lacking all putative glycosylation sites except for the N3 site, exhibited an attenuated phenotype (Table 2) with no considerable hematological changes in infected animals (FIG. 5), suggesting a significant role of E2-added oligosaccharides in viral virulence in swine.

To confirm the role of E2 glycosylation and further establish the impact of mutations at individual glycosylation sites in swine virulence, individual mutants were intranasally inoculated and evaluated relative to the parental virus. BICv exhibited a characteristic virulent phenotype (Table 2). Animals infected with N1v survived the infection and remained normal throughout the observation period (21 days). All animals infected with O1v, N2v, N3v, N4v, N5v, and N6v presented clinical signs of CSF starting 4 to 6 DPI, with clinical presentation and severity similar to those observed in animals inoculated with BICv. White blood cell and platelet counts dropped by 4 to 6 DPI in animals inoculated with O1v, N2v, N3v, N4v, N5v, and N6v, and BICv and kept declining until death, while a transient decrease was observed in animals inoculated with N1v (FIG. 5A). Viremia in N1v inoculated animals was transient (FIG. 5B) and significantly reduced by $10^4$ to $10^5$ from that observed in O1v, N2v, N3v, N4v, N5v, N6v, and BICv infected swine. A similar pattern was observed for nasal and tonsil samples (FIG. 5B), with no virus titers detected in tonsil samples obtained from N1v infected animals. In all cases partial nucleotide sequences of E2 protein from viruses recovered from infected animals were identical to those of stock viruses used for inoculation (data not shown).

TABLE 2

Swine survival and fever response following infection with CSFV E2 glycosylation mutants and parental BICv.

| Virus | Survivor/total | Mean time to death: Days ∀SD | Mean time of fever onset: Days ∀SD | Mean time of fever duration: Days ∀SD |
|---|---|---|---|---|
| BICv | 0/2 | 12 (0.00) | 5 (1.41) | 6.5 (0.70) |
| O1v | 0/2 | 9.5 (2.12) | 5 (0.00) | 4.5 (2.12) |
| N1v | 6/6 | — | — | — |
| N2v | 0/2 | 11(0.00) | 4.5 (0.70) | 5.5 (2.12) |
| N3v | 0/2 | 12 (5.65) | 6 (2.82) | 6 (2.82) |
| N4v | 0/2 | 16 (0.00) | 6 (1.41) | 8 (1.41) |
| N5v | 0/2 | 8.5 (0.70) | 5 (0.00) | 3.5 (0.70) |
| N6v | 0/2 | 8 (0.00) | 5 (0.00) | 2.5 (0.70) |
| ΔO1N1-N6/N3v | 2/2 | — | — | — |

The capability of N1v to establish a systemic infection in intranasally inoculated animals was compared with that of virulent parental virus BICv. Randomly selected animals were euthanized at 2, 4, 6, 8 and 12 DPI (one animal/time point/group) and virus titration was performed in collected tissues (tonsil, mandibular lymph nodes, kidney and spleen).

Titers measured in those tissue samples are shown in Table 3. In vivo replication of N1v were transient in tonsils with titers reduced up to $10^2$ to $10^5$, depending on the time post-infection, relative to those of BICv. Differences between N1v and BICv virus titers were also observed in mandibular lymph nodes and spleen, and no mutant virus was detected in kidney, indicating a limited capability of N1v to spread within the host.

TABLE 3

Titers of virus in tissues after intranasal inoculation with mutant N1v and parental BICv.

| | | $Log_{10}$ $TCID_{50}$/g in: | | | |
|---|---|---|---|---|---|
| Virus | DPI | Tonsil | Mandibular Lymph Node | Spleen | Kidney |
| N1v | 2 | n.d.* | 2.13 | n.d | n.d. |
| | 4 | 4.3 | n.d. | n.d. | 1.97 |
| | 6 | 4.8 | 4.3 | 4.47 | 2.47 |
| | 8 | 2.8 | 2.13 | 1.97 | n.d. |
| | 12 | n.d. | n.d. | n.d. | n.d. |
| BICv | 2 | n.d. | n.d. | n.d. | n.d. |
| | 4 | 6.3 | 4.13 | 4.8 | 2.8 |
| | 6 | 7.3 | 5.63 | 6.3 | 5.13 |
| | 8 | 7.8 | 7.8 | 7.47 | 7.47 |
| | 12 | D# | D | D | D |

*n.d. (not detectable): virus titers equal or less than 1.8 $TCID_{50}$ ($log_{10}$).
#D, animals in this group were all dead by this time point.

Example 7

Immunization, Challenge, and Clinical Analysis

For protection studies, 12 pigs were randomly allocated into 3 groups of 4 animals each Pigs in groups 1 and 2 were inoculated with N1v or N1E0/1v, and pigs in group 3 were mock infected. At 3 DPI (group 1) or 28 DPI (group 2), animals were challenged with BICv along with animals in group 3. Clinical signs and body temperature were recorded daily throughout the experiment as described above. Blood, serum, nasal swabs and tonsil scrapings were collected at times post-challenge, with blood obtained from the anterior vena cava in EDTA-containing tubes (Vacutainer) for total and differential white blood cell counts. Total and differential white blood cell and platelet counts were obtained using a Beckman Coulter ACT (Beckman, Coulter, Calif.).

Figure 6:
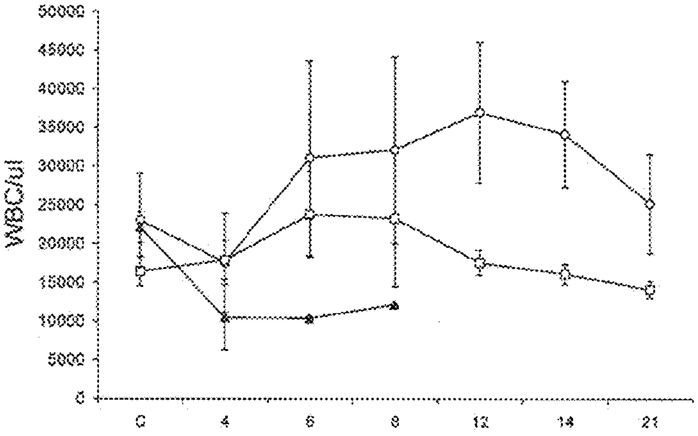
FIGS. 6A and 6B show the peripheral white blood cell (FIG. 6A) and the platelet counts (FIG. 6B) in pigs mock-vaccinated or vaccinated with N1v and challenged at 3 or 28 DPI with BICv. Values for control, mock-vaccinated and challenged animals are represented with filled triangles. Counts are expressed as numbers/ul and represent the mean and standard deviations from four individuals.
Figure 6:
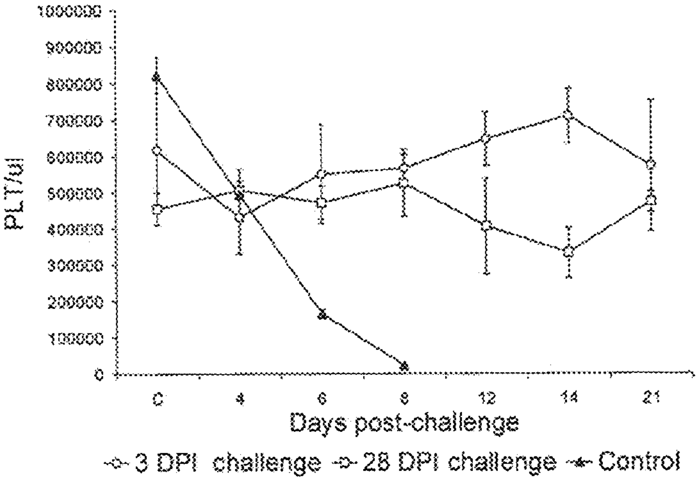

The limited in vivo replication kinetics of N1v is similar to that observed with CSICv (Risatti et al. 2005a, supra), a CSFV vaccine strain. However, restricted viral in vivo replication could also impair protection against wild-type virus infection. Thus, the ability of N1v to induce protection against virulent BICv was assessed in early and late vaccination-exposure experiments. Groups of pigs (n=4) were intranasally inoculated with N1v and challenged at 3 or 28 DPI. Mock-vaccinated control pig groups receiving BICv only (n=3) developed anorexia, depression, and fever by 4 days post-challenge (DPC), and a marked reduction of circulating leukocytes and platelets by 4 DPC (FIG. 6), and died or were euthanized in extremis by 9 DPC. Notably, N1v induced complete protection by 3 DPI. All pigs survived infection and remained clinically normal, without significant changes in their hematological values (FIG. 6). Pigs challenged at 28 days post N1v infection were also protected, remaining clinically normal, without alterations of hematological profiles after challenge (FIG. 6).

Viremia and virus shedding of vaccinated-exposed animals was examined at 4, 6, 8, 12, 14 and 21 DPC (Table 4). As expected, in mock-vaccinated control animals, viremia was observed by 4 DPC, with virus titers remaining high by 8 DPC (approximately $10^{7.8}$ $TCID_{50}$/ml) in the surviving pigs. Furthermore, virus was detected in nasal swabs and tonsil scrapings of these animals after 4 DPC. Conversely, viremia was detected by 4 DPC in animals challenged at 3 DPI (Table 4), but no virus was detected in nasal or tonsil samples in this group during the observation period. Virus was not detected in clinical samples obtained from pigs challenged at 28 DPI. Even though N1v showed a limited in vivo growth, a solid protection was induced shortly after vaccination.

TABLE 4

Detection of virus in nasal swabs, tonsil scrapings, and blood samples obtained after challenge of N1v-vaccinated animals with virulent BICv.

| Challenge | | Days Post-Challenge | | | | | | |
|---|---|---|---|---|---|---|---|---|
| Group | Sample | 0 | 4 | 6 | 8 | 12 | 14 | 21 |
| 3 DPI | Nasal | 0/4* | 1/4 (1.9) | 1/4 (2.5) | 1/4 (3.1) | 0/4 | 0/4 | 0/4 |
| | Tonsil | 0/4 | 1/2 (2.1) | 1/4 (2.8) | 2/4 (2.7) | 0/4 | 0/4 | 0/4 |
| | Blood | 0/4 | 1/2 (2.9)# | 3/4 (4) | 1/4 (4.8) | 0/4 | 0/4 | 0/4 |
| 28 DPI | Nasal | 0/4 | 0/4 | 0/4 | 0/4 | 0/4 | 0/4 | 0/4 |
| | Tonsil | 0/4 | 0/4 | 0/4 | 0/4 | 0/4 | 0/4 | 0/4 |
| | Blood | 0/4 | 0/4 | 0/4 | 0/4 | 0/4 | 0/4 | 0/4 |
| Control | Nasal | 0/2 | 0/2 | 2/2 (2.1) | 2/2 (5.1) | D | | |
| | Tonsil | 0/2 | 1/2 (2.1) | 2/2 (2.7) | 2/2 (4.1) | | | |
| | Blood | 0/2 | 1/2 (2.2) | 2/2 (6.4) | 2/2 (7.2) | | | |

*Number of animals positive for isolated virus over total number of challenged animals.
#Number in parentheses indicates average virus liters expressed as $log_{10}$ $TCID_{50}$/ml for four animals;
D Animals in this group were all dead by this time point Additionally, the ability of a virus containing alterations of the N1 sites in glycoproteins E0 and E2 (N1 E0/2v) of inducing protection against the virulent challenge was assessed in early and late vaccination-exposure experiments. As with N1v, Groups of pigs (n=4) were intramuscularly inoculated with N1 E0/2v and challenged at 3 or 28 DPI. Mock-vaccinated control pigs receiving BICv only (n=2) developed anorexia, depression, and fever by 4-10 days post-challenge (DPC) (Table 5), and a marked reduction of circulating leukocytes and platelets by 4 DPC (data not shown), and died or were euthanized in extremis by 11-17 DPC. N1E0/2v induced complete protection by 3 and 28 DPI. All pigs survived infection and remained clinically normal (Table 5), without significant changes in their hematological values (data not shown).

TABLE 5

Swine survival and fever response in N1E0/2v vaccinated animals following challenge with parental BICv.

| *N1E0/2 infected/ | | | Fever | |
|---|---|---|---|---|
| Challenged with BICv at 3 or 28 DPI | No. of Survivors/ Total no. | Mean time To Death (Days ± SD) | No. of Days To Onset (Days ± SD) | Duration-No. of Days (Days ± SD) |
| N1E0/2v/3 DPI | 4/4 | — | — | — |
| N1E0/2v/28 DPI | 4/4 | — | — | — |
| Mock/3 DPI | 0/2 | 17 (1.41) | 10 (0.0) | 7 (1.41) |
| Mock/28 DPI | 0/2 | 11.5 (4.95) | 3.5 (1.41) | 6.5 (3.54) |

*animals were intramuscularly infected with $10^5$ $TCID_{50}$ of N1E0/2v and challenged either at 3 or 28 DPI with $10^5$ $TCID_{50}$ of BICv by the intranasal route.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A genetically modified recombinant classical swine fever virus (CSFV) mutant of a highly pathogenic native Brescia strain, said mutant, N1E0/2v, comprising a cDNA encoding two mutations, wherein one of the mutations is in CSFV E0 glycoprotein, which is presented in the N1 site of the E0 glycoprotein, and the glycosylated amino acid asparagine at position 269 of the E0 glycoprotein is altered to the non-glycosylated amino acid, alanine; and another of the mutations is in CSFV E2 glycoprotein, which is presented in N1 site of the E2 glycoprotein, and the glycosylated amino acid asparagine at position 116 of the E2 is altered to the non-glycosylated amino acid alanine, resulting in attenuation of the CSFV mutant.

2. The recombinant CSFV mutant of claim 1 comprising 2 cDNA having the sequence SEQ ID NO: 3 wherein the codon of nucleotides 1178, 1179 and 1180 encodes the alanine of said position 269 of CSFV glycoprotein and the codon of nucleotides 2786, 2787 and 2789 encodes the alanine of said position 116 of CSFV E2 glycoprotein.

3. The recombinant CSFV mutant according to claim 1 wherein the CSFV mutant comprises additional attenuating mutations.

4. A vaccine composition comprising the recombinant CSFV mutant according to any one of claims 1, 2 and 3.

5. An isolated cell infected with the CSFV mutant of any one of claims 1, 2 and 3.

6. A method of immunizing swine against CSF, comprising administering to swine a live attenuated CSF vaccine comprising a recombinant CSFV mutant according to any one of claims 1 and 2.

7. A method for the protection of swine against CSF, comprising administering to swine a live attenuated CSF vaccine comprising a recombinant CSFV mutant according to any one of claims 1 and 2 in an amount effective to protect said swine from clinical CSF.

8. A plasmid capable of directly transfecting a suitable host cell and expressing a genetically modified CSFV from the suitable host cell so transfected, which plasmid comprises a) the DNA sequence of claim 2, and b) a promoter capable of transcribing said infectious RNA molecule in said suitable host cell.

9. A method for generating a genetically modified CSFV, which method comprises transfecting a suitable host cell with a plasmid according to 8 encoding the genetically modified CSFV and obtaining the genetically modified CSFV generated by the transfected host cell.

* * * * *